(12) United States Patent
Zemel et al.

(10) Patent No.: US 9,737,501 B2
(45) Date of Patent: Aug. 22, 2017

(54) COMPOSITIONS, METHOD, AND KITS FOR TREATING PULMONARY CONDITIONS

(71) Applicant: NUSIRT SCIENCES, INC., Nashville, TN (US)

(72) Inventors: Michael Zemel, Knoxville, TN (US); Brooke Baggett, Knoxville, TN (US); Antje Bruckbauer, Knoxville, TN (US)

(73) Assignee: NuSirt Sciences, Inc., Nashville, TN (US)

( * ) Notice: Subject to any disclaimer, the term of this patent is extended or adjusted under 35 U.S.C. 154(b) by 23 days.

(21) Appl. No.: 14/339,096

(22) Filed: Jul. 23, 2014

(65) Prior Publication Data

US 2015/0018375 A1    Jan. 15, 2015

Related U.S. Application Data

(63) Continuation-in-part of application No. PCT/US2014/011531, filed on Jan. 14, 2014.

(60) Provisional application No. 61/752,909, filed on Jan. 15, 2013.

(51) Int. Cl.
| | |
|---|---|
| *A01N 43/90* | (2006.01) |
| *A61K 31/52* | (2006.01) |
| *A61K 31/198* | (2006.01) |
| *A61K 31/05* | (2006.01) |
| *A61K 31/19* | (2006.01) |
| *A61K 31/522* | (2006.01) |

(52) U.S. Cl.
CPC ............ *A61K 31/198* (2013.01); *A61K 31/05* (2013.01); *A61K 31/19* (2013.01); *A61K 31/522* (2013.01)

(58) Field of Classification Search
None
See application file for complete search history.

(56) References Cited

U.S. PATENT DOCUMENTS

| | | | |
|---|---|---|---|
| 4,606,909 A | 8/1986 | Bechgaard et al. | |
| 4,769,027 A | 9/1988 | Baker et al. | |
| 4,803,080 A | 2/1989 | Benedikt et al. | |
| 4,837,032 A | 6/1989 | Ortega | |
| 4,897,268 A | 1/1990 | Tice et al. | |
| 5,069,204 A | 12/1991 | Smith et al. | |
| 5,229,390 A * | 7/1993 | Moriyama et al. | 514/263.32 |
| 5,395,626 A | 3/1995 | Kotwal et al. | |
| 6,426,091 B1 | 7/2002 | Okumura et al. | |
| 6,635,268 B2 | 10/2003 | Peery et al. | |
| 6,764,697 B1 | 7/2004 | Jao et al. | |
| 6,797,283 B1 | 9/2004 | Edgren et al. | |
| 6,878,751 B1 * | 4/2005 | Donnelly | A61K 47/48092 514/733 |
| 6,919,373 B1 | 7/2005 | Lam et al. | |
| 6,923,800 B2 | 8/2005 | Chen et al. | |
| 6,929,803 B2 | 8/2005 | Wong et al. | |
| 6,939,556 B2 | 9/2005 | Lautenbach | |
| 7,109,198 B2 | 9/2006 | Gadde et al. | |
| 7,870,856 B2 | 1/2011 | Boeck | |
| 2001/0051654 A1 | 12/2001 | Elliott et al. | |
| 2004/0105821 A1 | 6/2004 | Bernstein et al. | |
| 2005/0129620 A1 | 6/2005 | Clark | |
| 2005/0215640 A1 * | 9/2005 | Baxter | A61K 31/19 514/560 |
| 2006/0051416 A1 | 3/2006 | Rastogi et al. | |
| 2006/0173079 A1 | 8/2006 | Engelen et al. | |
| 2007/0065512 A1 | 3/2007 | Dedhiya et al. | |
| 2007/0141150 A1 * | 6/2007 | Kandarapu | A61K 9/1623 424/472 |
| 2009/0142336 A1 | 6/2009 | Walsh et al. | |
| 2010/0190744 A1 * | 7/2010 | Remmereit | 514/56 |
| 2010/0324002 A1 | 12/2010 | Fox et al. | |
| 2011/0064720 A1 | 3/2011 | Amato | |
| 2012/0225139 A1 | 9/2012 | Ferguson et al. | |
| 2013/0017283 A1 * | 1/2013 | Zemel et al. | 424/766 |
| 2015/0359771 A1 | 12/2015 | Zemel et al. | |

FOREIGN PATENT DOCUMENTS

| | | |
|---|---|---|
| EP | 2080508 A1 | 7/2009 |
| WO | WO 2013/012760 A1 | 1/2013 |
| WO | WO 2014/149280 A1 | 9/2014 |

OTHER PUBLICATIONS

Donovan (Natural News, 2008, http://www.naturalnews.com/025136_thiamine_diabetics_diabetic.html#).*
Leclercg-Meyer et al. (Endocrinology, 1985, 3, 1168-1174; abstract only).*
Zhou et al. (Respirology, 2006, 11, 603-610; abstract only).*
U.S. Appl. No. 13/549,381, filed Jul. 13, 2012, Zemel et al.
Bruckbauer, et al. Synergistic effects of leucine and resveratrol on insulin sensitivity and fat metabolism in adipocytes and mice. Nutr Metab (Lond). Aug. 22, 2012;9(1):77. doi: 10.1186/1743-7075-9-77.
International search report dated May 7, 2014 for PCT Application No. US2014/011531.
Zemel, et al. Effects of a leucine and pyridoxine-containing nutraceutical on fat oxidation, and oxidative and inflammatory stress in overweight and obese subjects. Nutrients. Jun. 2012;4(6):529-41. doi: 10.3390/nu4060529. Epub Jun. 15, 2012.
U.S. Appl. No. 14/761,283, filed Jul. 15, 2015, Zemel et al.
Amatruda, et al. Glucagon. Ch 7 from Ellenberg and Rifkin's Diabetes Mellitus. 6th ed. 2002; 97-115.
Yang, et a. Leucine metabolism in regulation of insulin secretion from pancreatic beta cells. Nutr Rev. May 2010;68(5):270-9. doi: 10.1111/j.1753-4887.2010.00282.x.

(Continued)

*Primary Examiner* — Dennis Heyer
*Assistant Examiner* — Daniel M Podgorski
(74) *Attorney, Agent, or Firm* — Wilson Sonsini Goodrich & Rosati

(57) ABSTRACT

Compositions, methods, and kits useful for treating pulmonary conditions are provided herein. Such compositions can contain synergizing amounts of a non-specific phosphodiesterase inhibitor, such as a methylxanthine, in combination with leucine and/or a leucine metabolite, and resveratrol.

25 Claims, 17 Drawing Sheets

(56) References Cited

OTHER PUBLICATIONS

Zhang, et al. Increasing dietary leucine intake reduces diet-induced obesity and improves glucose and cholesterol metabolism in mice via multimechanisms. Diabetes. Jun. 2007;56(6):1647-54. Epub Mar. 14, 2007.

European search report and opinion dated May 25, 2016 for EP Application No. 14740732.

Zhou, et al., Effect of resveratrol on chronic obstructive pulmonary disease in rats and its mechanism. Yao Xue Xue Bao. Feb. 2008;43(2):128-32.

* cited by examiner

COMPOSITIONS, METHOD, AND KITS FOR TREATING PULMONARY CONDITIONS

CROSS-REFERENCE

This application is a continuation-in-part of PCT Application No. PCT/US14/11531, filed Jan. 14, 2014, which claims benefit of priority to U.S. Provisional Application No. 61/752,909, filed Jan. 15, 2013, each of which is incorporated herein by reference in its entirety for all purposes.

BACKGROUND OF THE INVENTION

Pulmonary diseases or conditions span a range of lung-related diseases, including asthma and chronic obstructive pulmonary disease (COPD), which affect millions of people throughout the world.

For example, over 300 million people worldwide suffering from asthma. It is predicted that the prevalence will increase to about 400 million in the next decade. Asthma is a chronic airway disorder identified by recurrent wheeze and intermittent air flow limitation. It is characterized by airway inflammation, mucus hypersecretion, and airway hyperresponsiveness (AHR). Studies have shown that these clinical manifestations are, at least in part, inflammatory responses mediated by T-helper type 2 (Th2) cells together with mast cells, B cells and eosinophils, as well as a number of inflammatory cytokines and chemokines.

Currently, there are three anti-inflammatory agents for controlling asthma, which include inhaled steroids, cysteinyl-leukotriene receptor antagonist and cromolyn. However, the therapeutic efficacies of cysteinyl-leukotriene receptor antagonist and cromolyn are highly variable and may be limited to certain subgroup of patients. In addition, 5-10% of the asthmatics are not well-controlled by current drug treatment and they require oral steroids during exacerbation. Oral steroid usage is commonly associated with a diversity of adverse effects, most notably increases in appetite, stomach ulcers, difficulty sleeping (insomnia), changes in mood and behavior, flushing (redness) of the face, and short-term weight gain due to increased water retention. If taken for long periods of time, steroid use may lead to glaucoma, cataracts, high-blood pressure, heart disease, diabetes mellitus, obesity, acid reflux/GERD, osteoporosis, myopathy, increase in certain types of infections, and cushing syndrome.

COPD is a medical condition that is generally considered to include one or both of chronic bronchitis and emphysema. Chronic bronchitis is characterized by a persistent (such as more than one year) productive cough that is not due to a medically defined cause such as a microbial infection or carcinoma. Emphysema is an abnormal permanent non-uniform enlargement of air spaces distal to the terminal bronchioles, including destruction of the walls of the air spaces. COPD is caused by noxious particles or gas, most commonly from tobacco smoking, which triggers an abnormal inflammatory response in the lung. The natural course of COPD is characterized by occasional sudden worsening of symptoms called acute exacerbations, most of which are caused by infections or air pollution.

There is currently no cure for COPD and the only measures that have been shown to reduce mortality are smoking cessation and supplemental oxygen. COPD is treated with bronchodilators such as beta-2 agonists and/or anticholinergics. Beta-2 agonist stimulate beta-2 receptors while anticholinergics block stimulation from cholinergic nerves both are medicines that relax smooth muscle around the airways, increasing air flow. While these agents can ameliorate certain symptoms to some degree, they are not effective to halt progression of COPD.

Methylxanthines (a class of derivatives of xanthine and alkaloids) have often been used as bronchodilators. Methylxanthines relax smooth muscle, stimulate the central nervous system, stimulate cardiac muscle, and act on the kidneys to promote diuresis. Their usefulness in promoting relaxation of bronchial smooth muscle is of benefit in the management of asthma.

Methylxanthine theophylline is an established medicament for therapy of obstructive diseases of the respiratory tract. Theophylline is a competitive but non-selective inhibitor of several types of phosphodiesterases, the enzymes that degrade cAMP. Increased concentrations of cAMP may mediate the observed bronchodilation. Other proposed mechanisms of action of theophylline include inhibition of the release of intracellular calcium and competitive antagonism of the bronchoconstrictor adenosine.

Theophylline is a relatively low-cost treatment and can be administered in a sustained-release preparation that gives a duration of around 12 hours. However, theophylline has a number of side effects. The adverse gastrointestinal effects of theophylline include nausea, vomiting, abdominal pain, cramping, and diarrhea. Adverse central nervous system effects include insomnia, headache, dizziness, nervousness, and seizures, which are often more severe in children. Seizures may occur as the initial sign of theophylline toxicity without any other preceding signs and symptoms. Increased tremor in the patient's dominant hand has been reported. Cardiovascular and pulmonary adverse effects include tachycardia, arrhythmias, and tachypnea. Because of these toxicities, theophylline is often used as a second or third line asthma medication.

SUMMARY OF THE INVENTION

There remains a considerable need for low-cost therapy that can effectively and safely treat pulmonary conditions. The present invention addresses this need and provides related advantages as well.

The subject application provides compositions, methods, and kits useful for treating pulmonary conditions, including but not limited to asthma and chronic obstructive pulmonary disease. The subject compositions are particularly effective in reducing expression and/or secretion of an inflammatory marker or increasing the expression and/or secretion of an anti-inflammatory marker associated with the inflammatory responses elicited during onset of asthma or chronic obstructive pulmonary disease.

In one aspect of the invention, the subject composition comprises leucine and/or one or more leucine metabolites selected from the group consisting of keto-isocaproic acid (KIC), alpha-hydroxy-isocaproic acid, and hydroxymethyl-butyrate (HMB); and a methylxanthine, wherein the composition comprises at least about 250 mg of leucine and/or at least about 100 mg of the one or more leucine metabolites. In one aspect of the invention, the subject composition comprises leucine and/or one or more leucine metabolites selected from the group consisting of keto-isocaproic acid (KIC), alpha-hydroxy-isocaproic acid, and hydroxymethyl-butyrate (HMB); and a methylxanthine, wherein the composition comprises at least about 250 mg of leucine and/or at least about 10 or 50 mg of the one or more leucine metabolites. The composition can further comprise resveratrol.

In some embodiments, the composition comprises at least about 500 mg of leucine. The composition can comprise between about 250-1500 mg of leucine. The composition can comprise at least about 200 mg of leucine metabolites. The composition can comprise between about 100-750 mg of leucine metabolites. The composition can comprise between about 10-750 or 50-750 mg of leucine metabolites.

In another embodiment, the methylxanthine is selected from the group consisting of theophylline and theobromine. The methylxanthine may be present in a sub-therapeutic amount. The composition may comprise at least about 5 mg of theophylline. The composition can comprise between about 1-100 or 5-50 mg of theophylline. The composition can comprise a sub-therapeutic amount of theophylline.

In one embodiment, the composition comprises at least about 35 mg of resveratrol. The composition can comprise between about 5-500 or 30-250 mg of resveratrol.

In yet another embodiment, the composition is substantially free of non-branched amino acids. The amino acids in the composition can be substantially free of non-branched amino acids. The percent of non-branched amino acids relative to total amino acids in the composition can be less than about 0.1, 1, or 10%.

In some embodiments, the composition is a unit dosage. The composition can be formulated for oral dosing, inhalation, or intravenous delivery. The composition can be formulated for sustained release over a period of at least about 1, 4, 6, 12, 24, 36, or 48 hours. The sustained release formulations may maintain a desired circulating level of one or more components of the composition over a period of at least about 1, 4, 6, 12, 24, 36, or 48 hours. The sustained release formulations may effect a circulating level greater than a desired circulating level over a period of at least about 4, 6, 12, 24, 36, or 48 hours. The desired circulating level may be for any component of the compositions. The component may be a methylxanthine, such as theophylline. In some embodiments, the sustained release composition maintains the level of the methylxanthine at greater than about 1 $\mu$M for the specified time period. The sustained release formulation can effect a circulating level of methylxanthine in a subject that is greater than about 1 $\mu$M for the time period. The sustained release formulation can effect a circulating level of methylxanthine in a subject that is between about 1-10, 1-20, 1-30, or 1-40 $\mu$M for the time period.

In another aspect of the invention, the subject composition comprises (a) leucine and/or one or more leucine metabolites selected from the group consisting of keto-isocaproic acid (KIC), alpha-hydroxy-isocaproic acid, and hydroxymethylbutyrate (HMB); and (b) a methylxanthine, wherein the mass ratio of (a) to (b) is at least about 15, 25, 50, 75, or 100, and wherein the composition comprises at least about 5 mg of the methylxanthine. The composition can further comprise at least about 10 mg of resveratrol. In some embodiments, the methylxanthine is theophylline or theobromine. The composition may be formulated as a unit dosage.

In one aspect of the invention, the subject composition comprises (a) leucine and/or one or more leucine metabolites selected from the group consisting of keto-isocaproic acid (KIC), alpha-hydroxy-isocaproic acid, and hydroxymethylbutyrate (HMB); and (b) a methylxanthine, wherein the molar ratio of (a) to (b) is at least about 400, 500, 750, or 1000, and wherein the composition comprises at least about 0.05, 0.1, 0.5, 1, or 2 $\mu$g of the methylxanthine. The composition can comprise at least about 0.05, 0.1, 0.5, 1, or 2 mg of the methylxanthine. The composition can further comprise at least about 15, 30, 50, 100, or 500 $\mu$g of leucine.

The composition can further comprise at least about 5, 10, 15, 30, 50, 100, or 500 mg of leucine. The composition can further comprise at least about 0.01, 0.05, 0.1, 0.5, or 1 $\mu$g of resveratrol. The composition can further comprise at least about 0.01, 0.05, 0.1, 0.5, or 1 mg of resveratrol. In some embodiments, the methylxanthine is theophylline or theobromine. The composition may be formulated as a unit dosage for inhalation. The composition may be packaged in an inhaler. The inhaler can comprise at least about 20, 50, 200, or 1000 unit dosages of the composition.

In yet another aspect of the invention, the subject composition comprises (a) leucine; and (b) a methylxanthine, wherein component (a) and (b) are present in an amount effective to achieve a circulating level of about 0.3-2 mM leucine and about 0.5-10 $\mu$M methylxanthine in a subject. The amounts of (a) and (b) can be selected to induce a circulating level of about 0.7-2 mM leucine and about 0.7-3 $\mu$M methylxanthine in a subject. The subject can be a human, a domesticated animal, or a farm animal.

In another aspect, the subject composition comprises (a) leucine; and (b) a methylxanthine, wherein component (a) and (b) are present in an amount that is effective in improving a pulmonary condition by reducing expression level or secretion of one or more inflammatory markers in a lung endothelial cell selected from the group consisting of NF$\kappa$B, eotaxin, IL1-$\beta$, and IL6 or increasing expression level or secretion of one or more anti-inflammatory markers in a lung endothelial cell selected from the group consisting of adiponectin receptor 1 and adiponectin receptor 2.

In still another aspect, the subject composition comprises (a) leucine; and (b) a methylxanthine, wherein component (a) and (b) are present in an amount that is effective in reducing expression level or secretion of one or more inflammatory markers in a lung endothelial cell selected from the group consisting of NF$\kappa$B, eotaxin, IL1-$\beta$, and IL6, or increasing expression level or secretion of one or more anti-inflammatory markers in a lung endothelial cell selected from the group consisting of adiponectin receptor 1 and adiponectin receptor 2. The amount of (b) may be a sub-therapeutic amount. Alternatively, the amount of (b) may be less than an amount required to achieve a circulating level of about 40 $\mu$M.

The invention also provides for a method of treating pulmonary conditions in a subject in need of treatment comprising administering to the subject a composition of any one of the subject compositions.

In another aspect, the invention provides for a method of reducing expression level or secretion of an inflammatory marker selected from the group consisting of NF$\kappa$B, eotaxin, IL1-$\beta$, and IL6 or increasing expression level or secretion of an anti-inflammatory marker selected from the group consisting of adiponectin receptor 1 and adiponectin receptor 2, comprising contacting a lung endothelial cell with a composition of any one of the subject compositions described herein to effect said reduction or increase in expression level or secretion of said inflammatory marker or said anti-inflammatory marker. The subject can be a human, a domesticated animal, or a farm animal.

In yet another aspect, the invention provides for a kit comprising a multi-day supply of unit dosages of a subject composition described herein, and instructions directing the administration of said multi-day supply over a period of multiple days.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawing(s) of which:

DETAILED DESCRIPTION OF THE INVENTION

Figure 1:
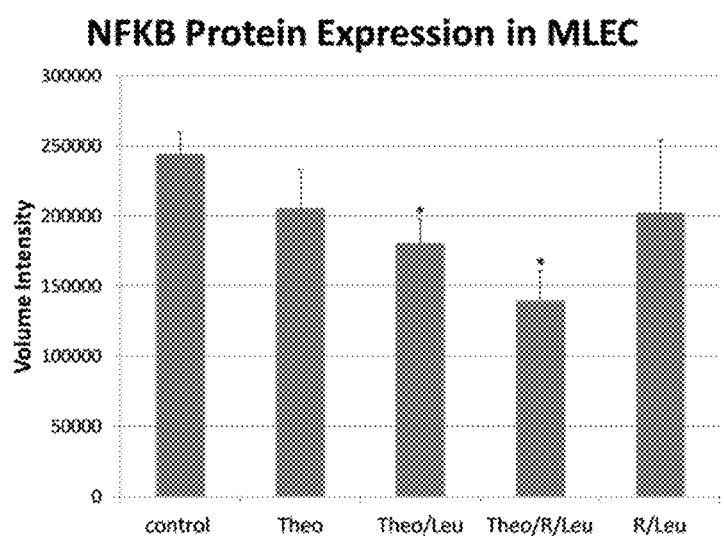
FIG. 1 depicts the interactive effects of theophylline with leucine and resveratrol on NFκB protein expression in mouse lung endothelial cells. *p<0.02 vs. control.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. Unless stated otherwise, the present invention is not limited by the illustrated ordering of acts or events, as some acts may occur in different orders and/or concurrently with other acts or events. Furthermore, not all illustrated acts or events are required to implement a methodology in accordance with the present invention. The concentration of various components in the disclosed compositions are exemplary and not meant to be limited to the recited concentration per se.

As used herein, the term "subject" or "individual" includes mammals. Non-limiting examples of mammals include humans and mice, including transgenic and non-transgenic mice. The methods described herein can be useful in both human therapeutics, pre-clinical, and veterinary applications. In some embodiments, the subject is a mammal, and in some embodiments, the subject is human. Other mammals include, and are not limited to, apes, chimpanzees, orangutans, monkeys; domesticated animals (pets) such as dogs, cats, guinea pigs, hamsters, mice, rats, rabbits, and ferrets; domesticated farm animals such as cows, buffalo, bison, horses, donkey, swine, sheep, and goats; or exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, pandas, giant pandas, hyena, seals, sea lions, and elephant seals.

The terms "administer", "administered", "administers" and "administering" are defined as the providing a composition to a subject via a route known in the art, including but not limited to intravenous, intraarterial, oral, nasal, inhaled, parenteral, buccal, topical, transdermal, rectal, intramuscular, subcutaneous, intraosseous, transmucosal, or intraperitoneal routes of administration. In certain embodiments of the subject application, oral routes of administering a composition may be preferred.

As used herein, "agent" or "biologically active agent" refers to a biological, pharmaceutical, or chemical compound or other moiety. Non-limiting examples include simple or complex organic or inorganic molecule, a peptide, a protein, a peptide nucleic acid (PNA), an oligonucleotide (including e.g., aptomer and polynucleotides), an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or down regulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

The term "isolated", as applied to a component of a subject composition, such component including, for example, a methylxanthine PDE inhibitor (including but not limited to theophylline and theobromine), leucine and leucine metabolites (including HMB, KIC and alpha-hydroxy-isocaproic acid), and resveratrol, refers to a preparation of the substance devoid of at least some of the other components that may also be present where the substance or a similar substance naturally occurs or is initially obtained from. Leucine or its metabolite when used in the subject composition is general in its free form and not as part of a polypeptide or a biomolecule. An isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichment of the embodiments of this invention are increasingly more preferred. Thus, for example, a 2-fold enrichment is preferred, 10-fold enrichment is more preferred, 100-fold enrichment is more preferred, 1000-fold enrichment is even more preferred. A substance can also be provided in an isolated state by a process of artificial assembly, such as by chemical synthesis.

A "modulator" of a pathway refers to a substance or agent which modulates the activity or expression of one or more cellular proteins mapped to the same specific signal transduction pathway. A modulator may augment or suppress the activity and/or expression level or pattern of a signaling molecule. A modulator can activate a component in a pathway by directly binding to the component. A modulator can also indirectly activate a component in a pathway by interacting with one or more associated components. The output of the pathway can be measured in terms of the expression or activity level of proteins. The expression level of a protein in a pathway can be reflected by levels of corresponding mRNA or related transcription factors as well as the level of the protein in a subcellular location. For instance, certain proteins are activated by translocating in or out of a specific subcellular component, including but not limited to nucleus, mitochondria, endosome, lysosome or other membraneous structure of a cell. The output of the pathway can also be measured in terms of physiological effects, such as mitochondrial biogenesis, fatty acid oxidation, or glucose uptake.

An "activator" refers to a modulator that influences a pathway in a manner that increases the pathway output. Activation of a particular target may be direct (e.g. by interaction with the target) or indirect (e.g. by interaction with a protein upstream of the target in a signaling pathway including the target).

A "suppressor" can be a modulator that influences a pathway in a manner that decreases pathway output.

The term "substantially free", as used herein, refers to compositions that have less than about 10%, less than about 5%, less than about 1%, less than about 0.5%, less than 0.1% or even less of a specified component. For example a composition that is substantially free of non-branched chain amino acids may have less than about 1% of the non-branched chain amino acid lysine. The percentage may be determined as a percent of the total composition or a percent of a subset of the composition. For example, a composition that is substantially free of non-branched chain amino acids may have less than 1% of the non-branched chain amino acids as a percent of the total composition, or as a percent of the amino acids in the composition. The percentages may be mass, molar, or volume percentages.

A "sub-therapeutic amount" of an agent, an activator or a therapy is an amount less than the effective amount of that agent, activator or therapy for an intended application, but when combined with an effective or sub-therapeutic amount of another agent or therapy can produce a desired result, due to, for example, synergy in the resulting efficacious effects, and/or reduced side effects.

A "synergistic" or "synergizing" effect can be such that the one or more effects of the combination compositions are greater than the one or more effects of each component alone, or they can be greater than the sum of the one or more effects of each component alone. The synergistic effect can be about, or greater than about 10, 20, 30, 50, 75, 100, 110, 120, 150, 200, 250, 350, or 500% or even more than the effect on a subject with one of the components alone, or the additive effects of each of the components when administered individually. The effect can be any of the measurable effects described herein.

Compositions

The subject compositions comprise a combination of (i) a non-specific PDE inhibitor, such as a methylxanthine, and (ii) leucine and/or one or more leucine metabolites. The compositions may further comprise resveratrol. The combination of these components can be useful for treating pulmonary conditions, including but not limited to asthma and chronic obstructive pulmonary disease. The combination can be particularly effective in reducing expression and/or secretion of an inflammatory marker or increasing expression and/or secretion of an anti-inflammatory marker associated with the inflammatory responses elicited during onset of asthma or chronic obstructive pulmonary disease. In some embodiments, the components are formulated to provide a synergistic effect, including but not limited to reduction in dosing amounts leading to reduced side effects to the subject and/or reduced cost of treatment. In other embodiments, the synergistic effect can allow for results that are not achievable through any other conventional treatments.

In one embodiment, the subject composition comprises leucine and/or one or more leucine metabolites selected from the group consisting of keto-isocaproic acid (KIC), alpha-hydroxy-isocaproic acid, and hydroxymethylbutyrate (HMB); and a methylxanthine, wherein the composition comprises at least about 250 mg of leucine and/or at least about 100 mg of the one or more leucine metabolites.

In another embodiment, the subject composition comprises (a) leucine and/or one or more leucine metabolites selected from the group consisting of keto-isocaproic acid (KIC), alpha-hydroxy-isocaproic acid, and hydroxymethylbutyrate (HMB); and (b) a methylxanthine, wherein the mass ratio of (a) to (b) is at least about 15, 25, 50, 75, or 100, and wherein the composition comprises at least about 5 mg of the methylxanthine. As described herein, a dosing of at least about 5 mg of methylxanthine can provide a sub-therapeutic dosing that can be effective when combined with a sufficient mass ratio of leucine or leucine metabolite.

In one aspect of the invention, the subject composition comprises (a) leucine and/or one or more leucine metabolites selected from the group consisting of keto-isocaproic acid (KIC), alpha-hydroxy-isocaproic acid, and hydroxymethylbutyrate (HMB); and (b) a methylxanthine, wherein the molar ratio of (a) to (b) is at least about 400, 500, 750, or 1000, and wherein the composition comprises at least about 0.05, 0.1, 0.5, 1, or 2 µg of the methylxanthine. The composition can comprise at least about 0.05, 0.1, 0.5, 1, or 2 mg of the methylxanthine. The composition can comprise at most about 0.001, 0.01, 0.1, 0.5, 1, 1.5, 2, 2.5, 3, 5, 10, or 20 grams of a methylxanthine, which may be theophylline and/or theobromine. The composition can further comprise at least about 15, 30, 50, 100, or 500 µg of leucine. The composition can further comprise at least about 5, 10, 15, 30, 50, 100, or 500 mg of leucine. The composition can comprise at most about 0.001, 0.01, 0.1, 0.5, 1, 1.5, 2, 2.5, 3, 5, 10, or 20 grams of leucine and/or a leucine metabolite. The composition can further comprise at least about 0.01, 0.05, 0.1, 0.5, or 1 µg of resveratrol. The composition can further comprise at least about 0.01, 0.05, 0.1, 0.5, or 1 mg of resveratrol. In some embodiments, the methylxanthine is theophylline or theobromine. The composition may be formulated as a unit dosage for inhalation.

In some embodiments, the composition is held within an inhaler designed to hold at least about 20, 50, 200, or 1000 unit dosages. The inhaler can comprise at least about 0.05, 0.1, 0.5, 1, or 2 µg of a methylxanthine per unit dose. The inhaler can comprise at least about 15, 30, 50, 100, or 500 of leucine per unit dose. The inhaler can comprise at least about 0.01, 0.05, 0.1, 0.5, or 1 µg of resveratrol per unit dose.

In yet another embodiment, the subject composition comprises (a) leucine; and (b) a methylxanthine, wherein component (a) and (b) are present in an amount effective to achieve a circulating level of about 0.3-2 mM leucine and about 0.5-10 µM methylxanthine in a subject. These targeted circulating levels correspond to treatment concentrations described herein (see Examples), which were shown to provide beneficial effects on pulmonary conditions in a subject.

In still another embodiment, the subject composition comprises (a) leucine; and (b) a methylxanthine, wherein component (a) and (b) are present in an amount that is effective in reducing expression level or secretion of one or more inflammatory markers in a lung endothelial cell selected from the group consisting of NFκB, eotaxin, IL1-β, and IL6, or in increase expression level or secretion of one or more anti-inflammatory markers selected from the group consisting of adiponectin receptor 1 and adiponectin receptor 2. The amount of (b) may be a sub-therapeutic amount. Alternatively, the amount of (b) may be less than an amount required to achieve a circulating level of about 40 µM. As described in the Examples, the combination of leucine and a methylxanthine can be combined to in amounts that have a beneficial effect on reducing expression level or secretion of one or more inflammatory markers in a lung endothelial cell such as NFκB, eotaxin, IL1-β, and IL6, or increasing the expression level or secretion of one or more anti-inflammatory markers selected from the group consisting of adiponectin receptor 1 and adiponectin receptor 2.

Phosphodiesterase Inhibitors

In some embodiments, the compositions can include a phosphodiesterase (PDE) inhibitor, such as a non-selective PDE inhibitor. PDE inhibitors can be naturally occurring or non-naturally occurring (e.g. manufactured), and may be provided in the form of a natural source comprising the PDE inhibitor, or an extract thereof (e.g. purified). Examples of non-selective PDE inhibitors include, but are not limited to, caffeine, theophylline, theobromine, 3-isobutyl-1-methylxanthine (IBMX), pentoxifylline (3,7-dihydro-3,7-dimethyl-1-(5oxohexyl)-1H-purine-2,6-dione), aminophylline, paraxanthine, and salts, derivatives, metabolites, catabolites, anabolites, precursors, and analogs thereof. Non-limiting examples of natural sources of PDE inhibitors include coffee, tea, guarana, verba mate, cocoa, and chocolate (e.g. dark chocolate). In various embodiments, compositions are formulated such that they do not contain (or exclude) one or more of the following ingredients: caffeine, green tea extract or extracts from guarana seed or guarana plants. Examples of phosphodiesterase inhibitors that may be used in a subject compositions are described in U.S. patent application Ser. No. 13/549,381, filed Jul. 13, 2012, which is herein incorporated by reference in its entirety.

The PDE inhibitors may also be methylxanthines. Examples of methylxanthines include caffeine, ephedrine, oxtriphylline, aminophylline, paraxanthine, IBMX, pentoxifylline, theobromine, and theophylline. Examples of aminophylline formulations include aminophylline Boehringer (Boehringer Ingelheim GmbH). Examples of ephedrine formulations include Bronkaid® (Bayer AG), broncholate (Sanofi-Aventis), Primatene® (Wyeth), tedral SA®, and marax (Pfizer Inc). Examples of theophylline formulations include euphyllin (Nycomed International Management GmbH), and theo-dur (Pfizer Inc, Teva Pharmaceutical Industries Ltd). Examples of oxtriphylline formulations include Choledyl SA (Pfizer Inc).

Leucine and Leucine Metabolites

The invention provides for compositions that include leucine and/or leucine metabolites. The leucine and/or leucine metabolites can be used in free form. The term "free," as used herein in reference to a component, indicates that the component is not incorporated into a larger molecular complex. For example a composition can include free leucine that is not incorporated in a protein or free hydroxymethylbutyrate. The leucine can be L-leucine.

Without being limited to theory, ingestion of branched chain amino acids, such as leucine, can stimulate sirtuin signaling, including Sirt1 and Sirt3, as well as AMPK signaling, one or more of which can favorably modulate inflammatory cytokine patterns. In some embodiments, any of the compositions described herein can include salts, derivatives, metabolites, catabolites, anabolites, precursors, and analogs of leucine. For example, the metabolites can include hydroxymethylbutyrate (HMB), keto-isocaproic acid (KIC), and keto isocaproate. The HMB can be in a variety of forms, including calcium 3-hydroxy-3-methylbutyrate hydrate.

In certain embodiments of the invention, any of the compositions disclosed herein can be formulated such that they do not contain (or exclude) one or more amino acids selected from the group consisting of lysine, glutamate, proline, arginine, valine, isoleucine, aspartic acid, asparagine, glycine, threonine, serine, phenylalanine, tyrosine, histidine, alanine, tryptophan, methionine, glutamine, taurine, carnitine, cystine and cysteine.

In some embodiments, the compositions may be substantially free of one or more, or all of non-branched chain amino acids. For example, the compositions can be free of alanine, arginine, asparagine, aspartic acid, cysteine, glutamic acid, glutamine, glycine, histidine, lysine, methionine, phenylalanine, proline, serine, threonine, tryptophan, and/or tyrosine. In some embodiments, the compositions may be substantially free of isoleucine and/or valine. The compositions can be substantially free of any non-branched chain amino acids. The mass or molar amount of a non-branched chain amino acid can be less than about 0.01, 0.1, 0.5, 1, 2, 5, or 10% of the total composition or of the total amino acids in the composition.

Pharmaceutically Active Agents

The subject compositions can further include one or more pharmaceutically active agents other than a methylxanthine PDE inhibitor. Examples of therapeutically active agents include ibuprofen, aldoril, and gemfebrozil, verapamil, maxzide, diclofenac and metrolol, maproltiline, triazolam and minoxidil. For example, the combination compositions can comprise a pharmaceutically active anti-diabetic agent, weight loss agent, or calcium regulation agent. U.S. Pat. No. 7,109,198 and U.S. Patent Application No. 20090142336 describe a variety of pharmaceutically active agents or therapeutically active agents suitable for inclusion in a combination composition described herein. Examples of anti-diabetic agents include biguanides (such as metformin), thiazoladinediones and meglitinides (such as repaglinide, pioglitazone, and rosiglitazone), alpha glucosidease inhibitors (such as acarbose), sulfonylureas (such as tolbutamide, acetohexamide, tolazamide, chlorpropamide, glipizide, glyburide, glimepiride, gliclazide), incretins, ergot alkaloids (such as bromocriptine), and DPP inhibitors (such as sitagliptin, vildagliptin, saxagliptin, lingliptin, dutogliptin, gemigliptin, alogliptin, and berberine). The anti-diabetic agent can be an oral anti-diabetic agent. The anti-diabetic agent can also be injectable anti-diabetic drugs, including insulin, amylin analogues (such as pramlintide), and inretin mimetics (such as exenatide and liraglutide). Examples of anti-obesity therapeutic agents include lipase inhibitors (such as Orlistat), dopaminergic, noradrenergic, and serotoninergic compounds, cannabinoid receptor antagonists (such as rimonabant), exenatide, pramlintide, and CNS agents (such as topimerate). These examples are provided for discussion purposes only, and are intended to demonstrate the broad scope of applicability of the invention to a wide variety of drugs. It is not meant to limit the scope of the invention in any way.

In some embodiments, a methylxanthine PDE inhibitor can be combined with a pair of pharmaceutically active agents as follow: glipizide and metformin; glyburide and metformin; pioglitazone and glimepiride; pioglitazone and metformin; repaglinide and metformin; rosiglitazone and glimepiride; rosiglitazone and metformin; and sitagliptin and metformin.

The amount of pharmaceutical agent, or any other component used in a combination composition described herein, can be a used in an amount that is sub-therapeutic. In some embodiments, using sub-therapeutic amounts of an agent or component can reduce the side-effects of the agent. Use of sub-therapeutic amounts can still be effective, particularly when used in synergy with other agents or components.

A sub-therapeutic amount of the agent or component can be such that it is an amount below which would be considered therapeutic. For example, FDA guidelines can suggest a specified level of dosing to treat a particular condition, and a sub-therapeutic amount would be any level that is below the FDA suggested dosing level. The sub-therapeutic amount can be about 1, 5, 10, 15, 20, 25, 30, 35, 50, 75, 90, or 95% less than the amount that is considered to be a therapeutic amount. The therapeutic amount can be assessed for individual subjects, or for groups of subjects. The group of subjects can be all potential subjects, or subjects having a particular characteristic such as age, weight, race, gender, or physical activity level.

In the case of metformin hydrochloride, the physician suggested starting dose is 1000 mg daily, with subject specific dosing having a range of 500 mg to a maximum of 2500 mg daily (metformin hydrochloride extended-release tablets label www.accessdata.fda.gov/drugsatfda_docs/label/2008/021574s0101bl.pdf). The particular dosing for a subject can be determined by a clinician by titrating the dose and measuring the therapeutic response. The therapeutic dosing level can be determined by measuring fasting plasma glucose levels and measuring glycosylated hemoglobin. A sub-therapeutic amount can be any level that would be below the recommended dosing of metformin. For example, if a subject's therapeutic dosing level is determined to be 700 mg daily, a dose of 600 mg would be a sub-therapeutic amount. Alternatively, a sub-therapeutic amount can be determined relative to a group of subjects rather than an individual subject. For example, if the average therapeutic amount of metformin for subjects with weights over 300 lbs is 2000 mg, then a sub-therapeutic amount can be any amount below 2000 mg. In some embodiments, the dosing can be recommended by a healthcare provider including, but not limited to a patient's physician, nurse, nutritionist, pharmacist, or other health care professional. A health care professional may include a person or entity that is associated with the health care system. Examples of health care professionals may include surgeons, dentists, audiologists, speech pathologists, physicians (including general practitioners and specialists), physician assistants, nurses, midwives, pharmaconomists/pharmacists, dietitians, therapists, psychologists, physical therapists, phlebotomists, occupational therapists, optometrists, chiropractors, clinical officers, emergency medical technicians, paramedics, medical laboratory technicians, radiographers, medical prosthetic technicians social workers, and a wide variety of other human resources trained to provide some type of health care service.

In the case of a methylxanthine, the therapeutically effective level of the methylxanthine can be a circulating level between about 44-111 µM, which corresponds to about 10-20 µg/mL. A sub-therapeutic level of the methylxanthine, such as theophylline or theobromine, can be any circulating level below about 110, 100, 90, 80, 70, 60, 50, 44, 40, 35, 30, 20, 10, 5, or 1 µM or 10 µg/mL. The sub-therapeutic level of the methylxanthine, such as theophylline or theobromine, in a subject composition formulated for administration can be less than about 1, 5, 10, 20, 30, 50, 60, 70, 80, 90, 100, 125, 150, 175, 200, or 250 mg of the methylxanthine.

Any of the components described herein, including leucine, HMB, KIC, theophylline, theobromine, and resveratrol may be used in a subject composition in free form, purified from a natural source, and/or purified or prepared from a synthetic source. The natural source can be an animal source or plant source. The components may be pure to at least about 95, 97, 99, 99.5, 99.9, 99.99, or 99.999%.

Dosing Amounts

The invention provides for compositions that are combinations of isolated components, such as leucine, metabolites of leucine, such as HMB, methylxanthines, such as theophylline and theobromine, and resveratrol, that have been isolated from one or more sources. The invention provides for compositions that are enriched in leucine, metabolites of leucine, such as HMB, methylxanthines, such as theophylline and theobromine, and/or resveratrol. The components can be isolated from natural sources or created from synthetic sources and then enriched to increase the purity of the components. For example, theophylline can be created from a synthetic source and then enriched by one or more purification methods. Additionally, leucine can be isolated from a natural source and then enriched by one or more separations. The isolated and enriched components, such as sildenafil and leucine, can then be combined and formulated for administration to a subject.

In some embodiments, a composition comprises an amount of a methylxanthine or a PDE inhibitor (e.g., including but not limited to theophylline or theobromine). The amount of a methylxanthine may be a subtherapeutic amount, and/or an amount that is synergistic with one or more other compounds in the composition or one or more of the compounds administered simultaneously or in close temporal proximity with the composition. In some embodiments, the methylxanthine or PDE inhibitor is administered in a low dose, a medium dose, or a high dose, which describes the relationship between two doses, and generally do not define any particular dose range. The compositions can be administered to a subject such that the subject is administered a selected total daily dose of the composition. The total daily dose can be determined by the sum of doses administered over a 24 hour period.

A dose, which may be a unit dose, can comprise about, more than about, or less than about 200, 250, 400, 500, 600, 700, 800, 900, 1000, 1100, 1250, or more mg of leucine. The leucine may be free leucine. In some embodiments, a unit dose can comprise at least about 1000 mg of free leucine. The composition may comprise between about 10-1250, 200-1250, or 500-1250 mg of leucine. A dose, which may be a unit dose, can comprise about, more than about, or less than about 50, 100, 200, 250, 400, 500, 600, 700, 800, 900, 1000 or more mg of a leucine metabolite, such as HMB or KIC. The leucine metabolite may be a free leucine metabolite. The composition may comprise between about 10-900, 50-750, or 400-650 mg of the leucine metabolite, such as HMB or KIC. In some embodiments, a unit dose can comprise at least about 400 mg of free HMB.

In some embodiments, a daily dose of leucine can be about, less than about, or more than about 0.5-3.0 g/day (e.g. 0.5, 0.75, 1, 1.25, 1.5, 1.75, 2, 2.5, 3, or more g/day). A daily dose of HMB can be about, less than about, or more than about 0.20-3.0 g/day (e.g. 0.2, 0.4, 0.5, 0.75, 1, 1.5, 2, 2.5, 3, or more g/day). A daily dose of KIC can be about, less than about, or more than about 0.2-3.0 g/day (e.g. 0.2, 0.4, 0.5, 0.75, 1, 1.25, 1.5, 1.75, 2, 2.5, 3, or more g/day).

A dose, which may be a unit dose, can comprise a methylxanthine PDE inhibitor, such as theophylline or theobromine, that can be about, more than about, or less than about 0.01, 0.05, 0.1, 0.5, 1, 2, 5, 10, 20, 40, 60, 80, 100, 200, 400, 800, 1000, or 1500 mg of the methylxanthine PDE inhibitor. The composition can comprise between about 1-100, 5-50, or 10-20 mg of the methylxanthine, such as theophylline or theobromine. In some embodiments, a unit dose can comprise at least about 20 mg of theophylline or theobromine. In some embodiments, a unit dose can comprise at least about 20 mg of theophylline.

In some embodiments, the composition comprises both theophylline and theobromine, and the total amount of theophylline and theobromine can be about, more than about, or less than about 0.01, 0.05, 0.1, 0.5, 1, 2, 5, 10, 20, 40, 60, 80, 100, 200, 400, 800, 1000, or 1500 mg.

In other embodiments, a daily dose of a methylxanthine PDE inhibitor, such as theophylline or theobromine, can be about, more than about, or less than about 0.0001 mg/kg (mg of methylxanthine PDE inhibitor/kg of the subject receiving the dose), 0.005 mg/kg, 0.01 mg/kg, 0.5 mg/kg, 1 mg/kg, 2.5 mg/kg, 5 mg/kg, 7.5 mg/kg, 10 mg/kg, 12.5 mg/kg, 15 mg/kg, 20 mg/kg, 25 mg/kg, 50 mg/kg, 75 mg/kg, 100 mg/kg, or more.

A dose, which may be a unit dose, can comprise about, less than about, or more than about 1, 5, 10, 25, 35, 50, 51, 75, 100, 150, 200, 250, 300, 350, 400, 450, 500, or more mg of resveratrol. The composition may comprise between about 5-500, 30-250, or 35-100 mg of resveratrol. In some embodiments, a unit dose can comprise at least about 35 mg of resveratrol.

A daily low dose of resveratrol may comprise about, less than about, or more than about 0.5 mg/kg (mg of resveratrol/kg of the subject receiving the dose), 1 mg/kg, 2.5 mg/kg, 5 mg/kg, 7.5 mg/kg, 10 mg/kg, 12.5 mg/kg, 15 mg/kg, 20 mg/kg, 25 mg/kg, 50 mg/kg, 75 mg/kg, 100 mg/kg, or more; a daily medium dose of resveratrol may comprise about, less than about, or more than about 20 mg/kg, 25 mg/kg, 50 mg/kg, 75 mg/kg, 100 mg/kg, 125 mg/kg, 150 mg/kg, 175 mg/kg, 200 mg/kg, 250 mg/kg, or more; and a daily high dose of resveratrol may comprise about, less than about, or more than about 150 mg/kg, 175 mg/kg, 200 mg/kg, 225 mg/kg, 250 mg/kg, 300 mg/kg, 350 mg/kg, 400 mg/kg, or more.

In some embodiments, a composition, which may be formulated as a unit dose, can comprise (a) at least about 250 mg of leucine and/or at least about 100 mg of the one or more leucine metabolites and (b) comprises at least about 5 mg of a methylxanthine, such as theophylline or theobromine. The composition can further comprise at least about 35 mg of resveratrol.

In other embodiments, a composition, formulated as a unit dose, can comprise (a) between about 250-1500 mg of leucine or 100-750 mg of leucine metabolites and (b) 1-100 mg of a methylxanthine, such as theophylline or theobromine. In other embodiments, a composition, formulated as a unit dose, can comprise (a) between about 250-1500 mg of leucine, 10-750 mg of leucine metabolites, and/or 50-750 mg of leucine metabolites and (b) 1-100 mg of a methylxanthine, such as theophylline or theobromine. In some embodiments, the methylxanthine is theophylline and the composition comprises between about 5-50 mg of theophylline.

In some embodiments of the invention, the combination compositions can have a specified ratio of leucine amino acids and/or metabolites thereof to a methylxanthine PDE inhibitor. The specified ratio can provide for effective and/or synergistic treatment of pulmonary conditions, which, for example, may be measured as a reduction in NFκB protein expression, reduction in eotaxin secretion, reduction in IL1-β secretion, reduction in cellular IL6 content or secretion, reduction in adiponectin receptor 1 protein expression, and reduction in adiponectin receptor 2 protein expression. The ratio of leucine amino acids and/or metabolites thereof to a selective PDE inhibitor activator can be a mass ratio, a molar ratio, or a volume ratio.

In some embodiments, a composition can comprise (a) leucine and/or metabolites thereof (including HMB) and (b) a methylxanthine (including theophylline and theobromine), where the mass ratio of (a) to (b) can be about, less than about, or greater than about 0.1, 0.5, 1, 2, 5, 10, 15, 25, 50, 75, 100, 200, 300, 350, 400, 450, 500, 550, 600, 650, 700, 750, or 800. In some embodiments, the mass ratio of (a) to (b) is at least about 50. The composition can also comprise a minimal amount of methylxanthine, such as 5, 10 or 50 mg of the methylxanthine or a range of methylxanthine amount, such as 5-250 mg of methylxanthine.

In other embodiments, a composition can comprise (a) a methylxanthine PDE inhibitor (including theophylline and theobromine) and (b) resveratrol, where the mass ratio of (a) to (b) can be about, less than about, or greater than about 0.01, 0.05, 0.1, 0.5, 1, 2, 5, 10, 50, 100, 200, 300, 350, 400, 450, 500, 550, 600, or 650.

In some embodiments, the composition can be formulated for inhalation. The composition formulated for inhalation can be formulated as a liquid. The composition formulated for inhalation can be housed within an inhaler or nebulizer. The inhaler or nebulizer can hold at least about 10, 20, 40, 100, 500, 1000, or 2000 unit doses. A unit dose of a subject composition can have a volume of about or at least about 0.1, 0.25, 0.5, 1, or 5 mL. A unit dose of a subject composition can have a volume of about 0.5-5 mL, which may be administered in about 1-10 inhalations.

The composition formulated for inhalation can be formulated in a liquid form that comprises at least about, about, or less than about 0.25, 0.5, 0.75, 1 mM or more of leucine.

The composition formulated for inhalation can be formulated in a liquid form that comprises at least about, about, or less than about 0.1, 0.25, 0.5, 0.75, 1, 10, 20, 40, 60 $\mu$M or more of a leucine metabolite (such as HMB). The composition formulated for inhalation can be formulated in a liquid form that comprises at least about, about, or less than about 0.25, 0.5, 0.75, 1 mM or more of KIC.

The composition formulated for inhalation can be formulated in a liquid form that comprises at least about, about, or less than about 0.1, 0.25, 0.5, 0.75, 1, 10, 20, 40, 60, 80, 100, 120, 200, or 400 $\mu$M or more of the methylxanthine, such as theophylline or theobromine.

In some embodiments, the dosing of leucine, any metabolites of leucine, the PDE inhibitor (such as a methylxanthine), and resveratrol can be designed to achieve a specified physiological concentration or circulating level of leucine, metabolites of leucine, a methylxanthine and/or resveratrol. The physiological concentration can be a circulating level as measured in the blood stream of a subject. The subject can be a human or an animal. A selected dosing can be altered based on the characteristics of the subject, such as weight, rate of energy metabolism, genetics, ethnicity, height, or any other characteristic.

In some embodiments, a selected dose of a composition can be administered to a subject such that the subject achieves a desired circulating level of the composition. The desired circulating level of a component may be either a therapeutically effective level or a sub-therapeutic level.

The desired circulating level of the composition can be at least about 0.25, 0.5, 0.75, 1 mM or more of leucine. The desired circulating level of the composition can be at least about, less than about, or more than about 0.1, 0.25, 0.5, 0.75, 1, 10, 20, 40, 60 $\mu$M or more of a leucine metabolite (such as HMB). The desired circulating level of the composition can be at least about 0.25, 0.5, 0.75, 1 mM or more of KIC.

The desired circulating level of the composition can be at least about, less than about, or more than about 0.1, 0.25, 0.5, 0.75, 1, 10, 20, 40, 60, 80, 100, 120, 200, or 400 $\mu$M or more of the methylxanthine, such as theophylline or theobromine. The therapeutically effective level of theophylline can be between 44-111 $\mu$M, which corresponds to about 10-20 $\mu$g/mL. A sub-therapeutic level of theophylline can be any level below about 110, 100, 90, 80, 70, 60, 50, 44, 40, 35, 30, 20, 10, 5, or 1 $\mu$M or 10 $\mu$g/mL.

The desired circulating level of the composition can be at least about, less than about, or more than about 40, 60, 80, 100, 120, 150, 200, 300, 400, 800, 1600, 3000, or 5000 nM or more of the resveratrol. The selected dose can be chosen based on the characteristics of the subject, such as weight, height, ethnicity, or genetics.

In some embodiments, a composition comprises leucine and a methylxanthine in amounts that are effective to achieve a circulating level of about 0.3-2 mM leucine and about 0.5-10 $\mu$M methylxanthine in a subject.

An oral dosing of about 1,125 mg leucine can achieve a circulating level of leucine in a subject that is about 0.5 mM leucine. An oral dosing of about 300 mg leucine can achieve a circulating level of leucine in a subject that is about 0.25 mM.

An oral dosing of about 500 mg of HMB can achieve a circulating level of HMB in a subject that is about 5 $\mu$M HMB. An oral dosing of about 100 mg of HMB can achieve a circulating level of HMB in a subject that is about 0.8 $\mu$M HMB.

An oral dosing of about 1000 mg of theophylline can achieve a circulating level of theophylline in a subject that is about 110 $\mu$M theophylline. An oral dosing of about 25-30 mg of theophylline can achieve a circulating level of theophylline in a subject that is about 1 $\mu$M theophylline.

An oral dosing of about 1000 mg of theobromine can achieve a circulating level of theobromine in a subject that is about 110 $\mu$M theobromine. An oral dosing of about 25-30 mg of theobromine can achieve a circulating level of theophylline in a subject that is about 1 $\mu$M theobromine.

An oral dosing of about 1100 mg of resveratrol can achieve a circulating level of resveratrol in a subject that is about 0.5 mM resveratrol. An oral dosing of about 50 mg of resveratrol can achieve a circulating level of resveratrol in a subject that is about 200 nM resveratrol.

A dosing prepared for inhalation, which may be in liquid form, can be prepared at concentrations that are about 1, 1.5, 2, 2.5, or 3 times greater than the desired circulating concentration. For example, a formulation for inhalation may comprise about 0.5, 1, or 0.5-1 mM leucine, which can achieve a circulating level of leucine in the pulmonary tissue of a subject that is about 0.5 mM. A formulation for inhalation may comprise about 200, 400, or 200-400 nM resveratrol, which can achieve a circulating level of resveratrol in the pulmonary tissue of a subject that is about 200 nM. A formulation for inhalation may comprise about 1, 2, or 1-2 $\mu$M methylxanthine, which can achieve a circulating level of methylxanthine in the pulmonary tissue of a subject that is about 1 $\mu$M.

In some embodiments, the compositions can be formulated to achieve a desired circulating molar or mass ratios achieved after administration one or more compositions to a subject. The compositions can be a combination composition described herein. The molar ratio can be adjusted to account for the bioavailability, the uptake, and the metabolic processing of the one or more components of a combination composition. For example, if the bioavailability of a component is low, then the molar amount of a that component can be increased relative to other components in the combination composition. In some embodiments, the circulating molar or mass ratio is achieved within about 0.1, 0.5, 0.75, 1, 3, 5, or 10, 12, 24, or 48 hours after administration. The circulating molar or mass ratio can be maintained for a time period of about or greater than about 0.1, 1, 2, 5, 10, 12, 18, 24, 36, 48, 72, or 96 hours.

In some embodiments, the circulating molar ratio of leucine to a methylxanthine is about, less than about, or greater than about 1, 5, 10, 50, 100, 500, 1000, 5000, or 10000. In some embodiments, the circulating molar ratio of HMB to a methylxanthine is about or greater than about, or less than about 0.01, 0.05, 0.1, 0.5, 1, 5, 10, 50, or 100. In some embodiments, the circulating molar ratio of a methylxanthine to resveratrol is about, less than about, or greater than about 0.01, 0.05, 0.1, 0.5, 1, 5, 10, 50, or 100.

In some embodiments, a composition can comprise leucine and a methylxanthine in an amount that is effective in improving expression level or secretion of one or more inflammatory or anti-inflammatory markers in a cell selected from the group consisting of (a) NFκB protein expression, (b) eotaxin, (c) IL1-β, and (d) cellular IL6 content or secretion, (e) adiponectin receptor 1 protein expression, and (f) adiponectin receptor 2 protein expression. The composition can have an amount of methylxanthine that is less than the amount required to achieve a circulating level of about 40 µM. The composition can have an amount of methylxanthine that is effective to achieve a circulating level of about 0.1-40 µM. The amount of methylxanthine can also be greater than at least about 5 mg.

Dosing Forms

The compositions described herein can be compounded into a variety of different dosage forms. It can be used orally as a tablet, chewable tablet, caplets, capsule, soft gelatin capsules, lozenges or solution. Alternatively, the compositions can be formulated for inhalation or for intravenous delivery. The compositions can also be formulated as a nasal spray or for injection when in solution form. In some embodiments, the composition may be a liquid composition suitable for oral consumption.

Compositions formulated for inhalation may be packaged in an inhaler using techniques known in the art. An inhaler may be designed to dispense 0.25, 0.5, or 1 unit dose per inhalation. An inhaler may have a canister that holds the subject composition formulated for inhalation, a metering valve that allows for a metered quantity of the formulation to be dispensed with each actuation, and an actuator or mouthpiece that allows for the device to be operated and direct the subject composition into the subject's lungs. The formulated composition may include a liquefied gas propellant and possibly stabilizing excipients. The actuator may have a mating discharge nozzle that connects to the canister and a dust cap to prevent contamination of the actuator. Upon actuation, the subject composition may be volatized, which results in the formation of droplets of the subject composition. The droplets may rapidly evaporate resulting in micrometer-sized particles that are then inhaled by the subject.

A protocol for treatment via inhalation can include preparation of an aerosol having particle sizes of predetermined mass medial aerodynamic diameter (MMAD) between 3 and 8 µm delivered predominantly to the conducting and central lungs with or without overpressure using a jet, ultrasonic, electronic, vibrating porous plate, vibrating mesh nebulizer or energized dry powder inhaler. The jet or electronic nebulizers may further be combined with airflow control and the aerosol may be administered with overpressure. Nebulization devices and systems can allow for individualization of a delivered volumetric flow and vaporized aerosol together with a controlled airflow and with airflow overpressure conditions into a treatment protocol suitable for treatment of a variety of conditions including inflammatory pulmonary diseases.

The nebulizing system can comprise components, such as a jet or electronic nebulizer, a compressor and an electronic control means that cumulatively have properties that enable control of the breathing pattern by asserting a positive pressure (also called NIPPV) during the inhalation. This pressure can reduce the need for active breathing in COPD patients, which results in much more effective and easier lung delivery of the drugs combination to COPD patients having difficulty breathing or who are unable to breathe without oxygen.

Inhalers and methods for formulating compositions for inhalation are described in are described in U.S. Pat. Nos. 5,069,204, 7,870,856 and U.S. Patent Application No. 2010/0324002, which are incorporated herein by reference in its entirety.

Compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion, including liquid dosage forms (e.g., a suspension or slurry), and oral solid dosage forms (e.g., a tablet or bulk powder). Oral dosage forms may be formulated as tablets, pills, dragees, capsules, emulsions, lipophilic and hydrophilic suspensions, liquids, gels, syrups, slurries, suspensions and the like, for oral ingestion by an individual or a patient to be treated. Such dosage forms can be prepared by any of the methods of formulation. For example, the active ingredients can be brought into association with a carrier, which constitutes one or more necessary ingredients. Capsules suitable for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. Optionally, the inventive composition for oral use can be obtained by mixing a composition a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The liquid forms, in which the formulations disclosed herein may be incorporated for administration orally or by injection, include aqueous solution, suitably flavored syrups, aqueous or oil suspensions, and flavored emulsions with edible oils such as cottonseed oil, sesame oil, coconut oil, or peanut oil as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin.

A subject can be treated by combination of an injectable composition and an orally ingested composition.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

The preparation of pharmaceutical compositions of this invention, including oral and inhaled formulations, can be conducted in accordance with generally accepted procedures for the preparation of pharmaceutical preparations. See, for example, Remington's Pharmaceutical Sciences 18th Edition (1990), E. W. Martin ed., Mack Publishing Co., PA. Depending on the intended use and mode of administration, it may be desirable to process the magnesium-counter ion compound further in the preparation of pharmaceutical compositions. Appropriate processing may include mixing with appropriate non-toxic and non-interfering components, sterilizing, dividing into dose units, and enclosing in a delivery device.

This invention further encompasses anhydrous compositions and dosage forms comprising an active ingredient, since water can facilitate the degradation of some compounds. For example, water may be added (e.g., 5%) in the arts as a means of simulating long-term storage in order to determine characteristics such as shelf-life or the stability of formulations over time Anhydrous compositions and dosage forms of the invention can be prepared using anhydrous or low moisture containing ingredients and low moisture or low humidity conditions. Compositions and dosage forms of the invention which contain lactose can be made anhydrous if substantial contact with moisture and/or humidity during manufacturing, packaging, and/or storage is expected. An anhydrous composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An ingredient described herein can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Binders suitable for use in dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Lubricants which can be used to form compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the composition.

Lubricants can be also be used in conjunction with tissue barriers which include, but are not limited to, polysaccharides, polyglycans, seprafilm, interceed and hyaluronic acid.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Examples of suitable fillers for use in the compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof. A non-exhaustive list of examples of excipients includes monoglycerides, magnesium stearate, modified food starch, gelatin, microcrystalline cellulose, glycerin, stearic acid, silica, yellow beeswax, lecithin, hydroxypropylcellulose, croscarmellose sodium, and crospovidone.

The compositions described herein can also be formulated as extended-release, sustained-release or time-release such that one or more components are released over time. Delayed release can be achieved by formulating the one or more components in a matrix of a variety of materials or by microencapsulation. The compositions can be formulated to release one or more components over a time period of 1, 4, 6, 8, 12, 16, 20, 24, 36, or 48 hours. The release of the one or more components can be at a constant or changing rate.

In some embodiments, a subject composition described herein can be formulated in as matrix pellets in which particles of the subject composition are embedded in a matrix of water-insoluble plastic and which are enclosed by a membrane of water-insoluble plastic containing embedded particles of lactose, produces and maintains plasma levels of the subject composition within the targeted therapeutic range. In other embodiments, a subject composition can be formulated as a sustained release tablet obtained by coating core granules composed mainly of the subject composition with a layer of a coating film composed of a hydrophobic material and a plastic excipient and optionally containing an enteric polymer material to form coated granules and then by compressing the coated granules together with a disintegrating excipient. Sustained release formulations are described in U.S. Pat. Nos. 4,803,080, and 6,426,091, which are herein incorporated by reference in its entirety.

Using the controlled release dosage forms provided herein, the one or more cofactors can be released in its dosage form at a slower rate than observed for an immediate release formulation of the same quantity of components. In some embodiments, the rate of change in the biological sample measured as the change in concentration over a defined time period from administration to maximum concentration for an controlled release formulation is less than about 80%, 70%, 60%, 50%, 40%, 30%, 20%, or 10% of the rate of the immediate release formulation. Furthermore, in some embodiments, the rate of change in concentration over time is less than about 80%, 70%, 60%, 50%, 40%, 30%, 20%, or 10% of the rate for the immediate release formulation.

In some embodiments, the rate of change of concentration over time is reduced by increasing the time to maximum concentration in a relatively proportional manner. For example, a two-fold increase in the time to maximum concentration may reduce the rate of change in concentration by approximately a factor of 2. As a result, the one or more cofactors may be provided so that it reaches its maximum concentration at a rate that is significantly reduced over an immediate release dosage form. The compositions of the present invention may be formulated to provide a shift in maximum concentration by 24 hours, 16 hours, 8 hours, 4 hours, 2 hours, or at least 1 hour. The associated reduction in rate of change in concentration may be by a factor of about 0.05, 0.10, 0.25, 0.5 or at least 0.8. In certain embodiments, this is accomplished by releasing less than about 30%, 50%, 75%, 90%, or 95% of the one or more cofactors into the circulation within one hour of such administration.

Optionally, the controlled release formulations exhibit plasma concentration curves having initial (e.g., from 2 hours after administration to 4 hours after administration) slopes less than 75%, 50%, 40%, 30%, 20% or 10% of those for an immediate release formulation of the same dosage of the same cofactor.

In some embodiments, the rate of release of the cofactor as measured in dissolution studies is less than about 80%, 70%, 60% 50%, 40%, 30%, 20%, or 10% of the rate for an immediate release formulation of the same cofactor over the first 1, 2, 4, 6, 8, 10, or 12 hours.

The controlled release formulations provided herein can adopt a variety of formats. In some embodiments, the formulation is in an oral dosage form, including liquid dosage forms (e.g., a suspension or slurry), and oral solid dosage forms (e.g., a tablet or bulk powder), such as, but not limited to those, those described herein.

The controlled release tablet of a formulation disclosed herein can be of a matrix, reservoir or osmotic system. Although any of the three systems is suitable, the latter two systems can have more optimal capacity for encapsulating a relatively large mass, such as for the inclusion of a large amount of a single cofactor, or for inclusion of a plurality of cofactors, depending on the genetic makeup of the individual. In some embodiments, the slow-release tablet is based on a reservoir system, wherein the core containing the one or more cofactors is encapsulated by a porous membrane coating which, upon hydration, permits the one or more cofactors to diffuse through. Because the combined mass of the effective ingredients is generally in gram quantity, an efficient delivery system can provide optimal results.

Thus, tablets or pills can also be coated or otherwise compounded to provide a dosage form affording the advantage of prolonged action. For example, the tablet or pill can comprise an inner dosage an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings such materials including a number of polymeric acids and mixtures of polymeric acids with such materials as shellac, cetyl alcohol and cellulose acetate. In some embodiments, a formulation comprising a plurality of cofactors may have different cofactors released at different rates or at different times. For example, there can be additional layers of cofactors interspersed with enteric layers.

Methods of making sustained release tablets are known in the art, e.g., see U.S. Patent Publications 2006/051416 and 2007/0065512, or other references disclosed herein. Methods such as described in U.S. Pat. Nos. 4,606,909, 4,769,027, 4,897,268, and 5,395,626 can be used to prepare sustained release formulations of the one or more cofactors determined by the genetic makeup of an individual. In some embodiments, the formulation is prepared using OROS® technology, such as described in U.S. Pat. Nos. 6,919,373, 6,923,800, 6,929,803, and 6,939,556. Other methods, such as described in U.S. Pat. Nos. 6,797,283, 6,764,697, and 6,635,268, can also be used to prepare the formulations disclosed herein.

In some embodiments, the compositions can be formulated in a food composition. For example, the compositions can be a beverage or other liquids, solid food, semi-solid food, with or without a food carrier. For example, the compositions can include a black tea supplemented with any of the compositions described herein. The composition can be a dairy product supplemented any of the compositions described herein. In some embodiments, the compositions can be formulated in a food composition. For example, the compositions can comprise a beverage, solid food, semi-solid food, or a food carrier.

In some embodiments, liquid food carriers, such as in the form of beverages, such as supplemented juices, coffees, teas, sodas, flavored waters, and the like can be used. For example, the beverage can comprise the formulation as well as a liquid component, such as various deodorant or natural carbohydrates present in conventional beverages. Examples of natural carbohydrates include, but are not limited to, monosaccharides such as, glucose and fructose; disaccharides such as maltose and sucrose; conventional sugars, such as dextrin and cyclodextrin; and sugar alcohols, such as xylitol and erythritol. Natural deodorant such as taumatin, stevia extract, levaudioside A, glycyrrhizin, and synthetic deodorant such as saccharin and aspartame may also be used. Agents such as flavoring agents, coloring agents, and others can also be used. For example, pectic acid and the salt thereof, alginic acid and the salt thereof, organic acid, protective colloidal adhesive, pH controlling agent, stabilizer, a preservative, glycerin, alcohol, or carbonizing agents can also be used. Fruit and vegetables can also be used in preparing foods or beverages comprising the formulations discussed herein.

Alternatively, the compositions can be a snack bar supplemented with any of the compositions described herein. For example, the snack bar can be a chocolate bar, a granola bar, or a trail mix bar. In yet another embodiment, the present dietary supplement or food compositions are formulated to have suitable and desirable taste, texture, and viscosity for consumption. Any suitable food carrier can be used in the present food compositions. Food carriers of the present invention include practically any food product. Examples of such food carriers include, but are not limited to food bars (granola bars, protein bars, candy bars, etc.), cereal products (oatmeal, breakfast cereals, granola, etc.), bakery products (bread, donuts, crackers, bagels, pastries, cakes, etc.), beverages (milk-based beverage, sports drinks, fruit juices, alcoholic beverages, bottled waters), pastas, grains (rice, corn, oats, rye, wheat, flour, etc.), egg products, snacks (candy, chips, gum, chocolate, etc.), meats, fruits, and vegetables. In an embodiment, food carriers employed herein can mask the undesirable taste (e.g., bitterness). Where desired, the food composition presented herein exhibit more desirable textures and aromas than that of any of the components described herein. For example, liquid food carriers may be used according to the invention to obtain the present food compositions in the form of beverages, such as supplemented juices, coffees, teas, and the like. In other embodiments, solid food carriers may be used according to the invention to obtain the present food compositions in the form of meal replacements, such as supplemented snack bars, pasta, breads, and the like. In yet other embodiments, semi-solid food carriers may be used according to the invention to obtain the present food compositions in the form of gums, chewy candies or snacks, and the like.

The dosing of the combination compositions can be administered about, less than about, or more than about 1, 2, 3, 4, 5, 6, 7, 8, 9, 10 or more times a daily. A subject can receive dosing for a period of about, less than about, or greater than about 1, 2, 3, 4, 5, 6, 7, 8, 9, 10, 11, 12, 13, 14 or more days, weeks or months. A unit dose can be a fraction of the daily dose, such as the daily dose divided by the number of unit doses to be administered per day. A unit dose can be a fraction of the daily dose that is the daily dose divided by the number of unit doses to be administered per day and further divided by the number of unit doses (e.g. tablets) per administration. The number of unit doses per administration may be about, less than about, or more than about 1, 2, 3, 4, 5, 6, 7, 8, 9, 10, or more. The number of doses per day may be about, less than about, or more than about 1, 2, 3, 4, 5, 6, 7, 8, 9, 10, or more. The number of unit doses per day may be determined by dividing the daily dose by the unit dose, and may be about, less than about, or more than about 1, 2, 3, 4, 5, 6, 7, 8, 9, 10, 11, 12, 13, 14, 15, 6, 17, 18, 19, 20, or more unit doses per day. For example, a unit dose can be about ½, ⅓, ¼, ⅕, ⅙, ⅐, ⅛, ⅑, ⅒. A unit dose can be about one-third of the daily amount and administered to the subject three times daily. A unit dose can be about one-half of the daily amount and administered to the subject twice daily. A unit dose can be about one-fourth of the daily amount with two unit doses administered to the subject twice daily. In some embodiments, a unit dose comprises about, less than about, or more than about 50 mg resveratrol. In some embodiments, a unit dose comprises about, less than about, or more than about 550 mg leucine. In some embodiments, a unit dose comprises about, less than about, or more than about 200 mg of one or more leucine metabolites.

In some embodiments, a unit dose (e.g. a unit dose comprising one or more leucine metabolites, such as HMB) is administered as one unit dose two timer per day. A unit dose may comprise more than one capsule, tablet, vial, or entity.

Compositions disclosed herein can further comprise a flavorant and can be a solid, liquid, gel or emulsion.

Methods

The subject composition is particularly useful for ameliorating inflammatory responses elicited during onset of a pulmonary condition. In one embodiment, the invention provides for methods for reducing expression level or secretion of an inflammatory marker including but not limited to NFκB, eotaxin, IL1-β, and IL6, or increasing expression level or secretion of an anti-inflammatory marker including but not limited to adiponectin receptor 1 and adiponectin receptor 2, comprising contacting a lung endothelial cell with any of the subject compositions.

In various embodiments of the invention, a composition is administered to the subject in an amount that delivers synergizing amounts of leucine and/or a metabolite thereof, a methylxanthine PDE inhibitor, and/or resveratrol sufficient treat pulmonary conditions of the subject.

In some embodiments, the amounts of the methylxanthine, such as theophylline or theobromine, in the composition, if administered to a subject alone and without leucine, a leucine metabolite, or resveratrol, would cause no therapeutic effect in the subject. Additionally, the amounts of leucine, a leucine metabolite, or resveratrol, if administered to the subject without the methylxanthine, would have no therapeutic effect on the subject. However, when the methylxanthine is administered in conjunction with either leucine, a leucine metabolite, or resveratrol, a therapeutic effect is observed.

Accordingly, the invention provides a method for administering a composition comprising (a) leucine and/or one or more metabolites thereof and (b) a methylxanthine present in a sub-therapeutic amount, wherein the composition is effective in increasing treating pulmonary conditions by at least about 5 fold as compared to that of component (b) when it is used alone. The amount of leucine in the composition may also be a sub-therapeutic amount.

The invention also provides a method for administering a composition comprising (a) leucine and/or one or more metabolites thereof, (b) a methylxanthine present in a sub-therapeutic amount, and (c) resveratrol wherein the composition is effective in increasing treating pulmonary conditions by at least about 5 fold as compared to that of component (b) when it is being used alone.

Quantification of the therapeutic effect can show that the effect of a composition that comprises (a) a methylxanthine and (b) leucine or a leucine metabolite is greater than the predicted effect of administering (a) or (b) alone, assuming simple additive effects of (a) and (b), and thus the effect is synergistic. The synergistic effect can be quantified as the measured effect above the predicted simple additive effect of the components of the composition. For example, if administration of component (a) alone yields an effect of 10% relative to control, administration of component (b) alone yields an effect of 15% relative to control, and administration of a composition comprising both (a) and (b) yields an effect of 60% relative to control, the synergistic effect would be 60%-(15%+10%), or 35%.

At an in vitro level, the beneficial effects of the compositions can be measured on cultured lung endothelial cells, such as mouse primary lung endothelial cells, treated with corresponding concentrations of the compositions described herein. Analysis of the cells can allow for quantification of the beneficial effects. For example, western blots or ELISA assays can be performed to measure the quantity of (a) reduction in NFκB protein expression, (b) eotaxin secretion, (c) reduction in IL1-β secretion, (d) reduction in cellular IL6 content or secretion, (e) increase in adiponectin receptor 1 protein expression, and/or (f) increase in adiponectin receptor 2 protein expression in the cell as a result of treatment with a composition described herein.

Accordingly, the multi-component compositions described herein (such as theophylline/leucine, theophylline/leucine/resveratrol, theobromine/leucine, and theobromine/leucine/resveratrol) may have a synergistic effect on (a) reduction in NFκB protein expression, (b) eotaxin secretion, (c) reduction in IL1-β secretion, (d) reduction in cellular IL6 content or secretion, (e) increase in adiponectin receptor 1 protein expression, and/or (f) increase in adiponectin receptor 2 protein expression that is at least about 10, 20, 50, 100, 200, or 300%.

The output of the pathways and beneficial effects achieved in a subject can be measured using one or more methods, disclosed herein and/or known in the art. For example, measurements of COPD and asthma may be made using spirometry, refinements of spirometry, such as measurement of FEV6 and inspiratory capacity; measurements of functional outcomes, such as dyspnea indexes and exercise tests; and measurements of global-clinical outcomes, such as quality of life questionnaires and assessment of frequency and severity of acute exacerbations. In some embodiments, administration of the compositions described herein to a subject can effect spirometry values, lung capacity, and functional outcome measurements in the subject that are improvements of at least about 10, 30, 50, 100, 200 or 300% greater relative to no administration of the compositions or prior to administration of the compositions. The effects may also be synergistic effects of at least about 10, 20, 50, 100, 200, or 300%.

The compositions can be administered to a subject orally or by any other methods. Methods of oral administration include administering the composition as a liquid, a solid, or a semi-solid that can be taken in the form of a dietary supplement or a food stuff.

The compositions can be administered periodically. For example, the compositions can be administered one, two, three, four times a day, or even more frequent. The subject can be administered every 1, 2, 3, 4, 5, 6 or 7 days. In some embodiments, the compositions are administered three times daily. The administration can be concurrent with meal time of a subject. The period of treatment or diet supplementation can be for about 1, 2, 3, 4, 5, 6, 7, 8, or 9 days, 2 weeks, 1-11 months, or 1 year, 2 years, 5 years or even longer. In some embodiments of the invention, the dosages that are administered to a subject can change or remain constant over the period of treatment. For example, the daily dosing amounts can increase or decrease over the period of administration.

The length of the period of administration and/or the dosing amounts can be determined by a physician or any other type of clinician. The physician or clinician can observe the subject's response to the administered compositions and adjust the dosing based on the subject's performance. For example, dosing for subjects that show reduced effects in energy regulation can be increased to achieve desired results.

In some embodiments, the compositions administered to a subject can be optimized for a given subject. For example, the ratio of branched chain amino acids to a sirtuin pathway activator or the particular components in a combination composition can be adjusted. The ratio and/or particular components can be selected after evaluation of the subject after being administered one or more compositions with varying ratios of branched chain amino acids to a sirtuin pathway activator or varying combination composition components.

Another aspect of the invention provides for achieving desired effects in one or more subjects after administration of a combination composition described herein for a specified time period. For example, the beneficial effects of the compositions described herein can be observed after administration of the compositions to the subject for 1, 2, 3, 4, 6, 8, 10, 12, 24, or 52 weeks.

The invention provides for a method of treating subjects, comprising identifying a pool of subjects amenable to treatment. The identifying step can include one or more screening tests or assays. For example, subjects that are identified as asthmatic, diabetic or that have above average or significantly greater than average body mass indices and/or weight can be selected for treatment. The identifying step can include a genetic test that identifies one or more genetic variants that suggest that the subject is amenable to treatment. The identified subjects can then be treated with one or more compositions described herein. For example, they may be treated with a combination composition comprising a sirtuin pathway activator and a branched-chain amino acid.

The invention also provides for methods of manufacturing the compositions described herein. In some embodiments, the manufacture of a composition described herein comprises mixing or combining two or more components. These components can include a PDE inhibitor or sirtuin or AMPK pathway activator (such as a polyphenol or polyphenol precursor like resveratrol, or a methylxanthine), and leucine or metabolites thereof (such as HMB, or KIC). The amount or ratio of components can be that as described herein. For example, the mass ratio of leucine compared with resveratrol can be greater than about 80.

In some embodiments, the compositions can be combined or mixed with a pharmaceutically active agent, a carrier, and/or an excipient. Examples of such components are described herein. The combined compositions can be formed into a unit dosage as tablets, capsules, gel capsules, slow-release tablets, or the like.

In some embodiments, the composition is prepared such that a solid composition containing a substantially homogeneous mixture of the one or more components is achieved, such that the one or more components are dispersed evenly throughout the composition so that the composition may be readily subdivided into equally effective unit dosage forms such as tablets, pills and capsules.

Kits

The invention also provides kits. The kits include one or more compositions described herein, in suitable packaging, and may further comprise written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. A kit may comprise one or more unit doses described herein. In some embodiments, a kit comprises about, less than about, or more than about 1, 2, 3, 4, 5, 6, 7, 8, 9, 10, 11, 12, 13, 14, 15, 16, 17, 18, 19, 20, 30, 31, 60, 90, 120, 150, 180, 210, or more unit doses. Instructions for use can comprise dosing instructions, such as instructions to take 1, 2, 3, 4, 5, 6, 7, 8, 9, 10, or more unit doses 1, 2, 3, 4, 5, 6, 7, 8, 9, 10, or more times per day. For example, a kit may comprise a unit dose supplied as a tablet, with each tablet package separately, multiples of tablets packaged separately according to the number of unit doses per administration (e.g. pairs of tablets), or all tablets packaged together (e.g. in a bottle). As a further example, a kit may comprise a unit dose supplied as a bottled drink, the kit comprising 1, 2, 3, 4, 5, 6, 7, 8, 9, 10, 11, 12, 13, 14, 24, 28, 36, 48, 72, or more bottles.

The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

EXAMPLES

Example 1

Effects of Leucine, Theophylline, Theobromine and Resveratrol on Indicators of Pulmonary Conditions Techniques Cell Culture: Mouse primary lung endothelial cells (MLEC) were obtained from Cell Biologics (Chicago, Ill.). Cells were grown to confluence in T75 culture flasks pre-coated with 0.2% gelatin. Cells were grown in Dulbecco's modified eagle's medium (DMEM) containing a growth factor supplement (Cell Biologics # Ml 166) which included 5% fetal bovine serum (FBS), heparin, EGF, hydrocortisone, L-glutamine and antibiotics at 37° C. in 5% $CO_2$.

Adipocyte Conditioned Media Experiments: 3T3L1 adipocytes (passage 11 to 13) were grown and differentiated on 6-well plates and treated for 48 h with the treatments indicated in "Results". Media was then collected and pooled together for each treatment group. Pooled media was then used to treat confluent MLEC for 24 h in lieu of direct treatments. The MLEC media from each cell replicate was collected, aliquoted and stored in −20° C. for further experiments. The cells (MLEC and adipocytes) were washed once with ice-cold HBSS, then ice-cold RIPA buffer plus Protease and Phosphatase Inhibitors (Sigma) was added. The cell extract was then incubated on ice for 10 min, scraped, transferred to a new microcentrifuge tube, homogenized for 5 sec and then centrifuged for 10 min at 12,000×g at 4° C. Then the clear supernatant from each cell replicate was aliquoted and stored at −20° C. for further experiments, as indicated below.

Western Blot: NFκB and phospho-NFκB antibodies were obtained from Cell Signaling (Danvers, Mass.). Cells were treated as indicated in results and the cellular fractions were prepared using standard methods. Protein was measured by BCA kit (Thermo Scientific). For Western blot, 2 µg (for NFκB) or 4 µg (for phospho-NFκB) of protein from the cell lysate was resolved on 10% Tris/HCL polyacrylamide gels (Criterion precast gel, Bio-Rad Laboratories, Hercules, Calif.), transferred to PVDF membranes (NFκB and phospho-NFκB), incubated in blocking buffer (3% BSA in TBS) and then incubated with primary antibody, washed and incubated with secondary horseradish peroxidase-conjugated antibody. Visualization and chemiluminescent detection was conducted using BioRad ChemiDoc instrumentation and software (Bio-Rad Laboratories, Hercules, Calif.) and band intensity was assessed using Image Lab 4.0 (Bio-Rad Laboratories, Hercules, Calif.), with correction for background and loading controls. NFκB was detected at 60 kDA, and phospho-NFκB at 52-59 kDA.

Cytokines: Interleukin 1-β, eotaxin, and interleukin 6 were all measured via enzyme-linked immunosorbent assay using specific antibodies for each cytokine (Abcam, Cambridge, Mass.) and a horseradish peroxidase-based second antibody detection system, with chromogenic detection at 450 nm using a microplate reader (Synergy HT, BioTek Instruments, Winooski, Vt.).

Results

Mouse primary lung endothelial cells were treated with combinations of theophylline (1 µM), theobromine (1 µM), leucine (0.5 mM), and resveratrol (200 nM). Each of theophylline, theobromine, leucine, and resveratrol may be purchased from appropriate vendors in the form indicated or salts of the forms indicated. Following treatment, western blots or ELISA assays were performed on the MLEC to determine the level of various indicators of airway diseases, such as NFκB protein expression, eotaxin secretion, IL1-β secretion, cellular IL6 content or secretion, adiponectin receptor 1 protein expression, and adiponectin receptor 2 protein expression.

Treatment with 0.5 mM leucine corresponds to a circulating level of the same molarity achieved by orally administering about 1,125 mg of leucine to a human subject. Treatment with 0.25 mM leucine corresponds to a circulating level of the same molarity achieved by orally administering about 300 mg of leucine to a human subject.

Treatment with 110 µM theophylline corresponds to a circulating level of the same molarity achieved by orally administering about 1000 mg of theophylline to a human subject. Treatment with 1 µM theophylline corresponds to a circulating level of the same molarity achieved by orally administering about 25-30 mg of theophylline to a human subject.

Treatment with 0.5 mM resveratrol corresponds to a circulating level of the same molarity achieved by orally administering about 1100 mg of resveratrol to a human subject. Treatment with 200 nM resveratrol corresponds to a circulating level of the same molarity achieved by orally administering about 50 mg of resveratrol to a human subject.

Theophylline exerted no independent effect on NFκB protein expression relative to control (FIG. 1), but the theophylline/leucine and theophylline/leucine/resveratrol combinations resulted in significant reductions in NFκB ($p<0.02$); there was no significant difference between theophylline/leucine and theophylline/leucine/resveratrol treatments. Treatment of MLEC with a combination of resveratrol and leucine had no effect on the NFκB levels relative to control. Phospho-NFκB exhibited similar trends. As shown by this data, the combination of theophylline with leucine and theophylline with leucine and resveratrol has a synergistic effect because treatment with alone with (a) theophylline or (b) leucine and resveratrol had no effect on NFκB or phospho-NFκB levels. The synergistic effect of combining theophylline with leucine or leucine and resveratrol was an improvement of at least about 22% relative to baseline (treatment with theophylline alone or leucine and resveratrol alone).

Figure 2:
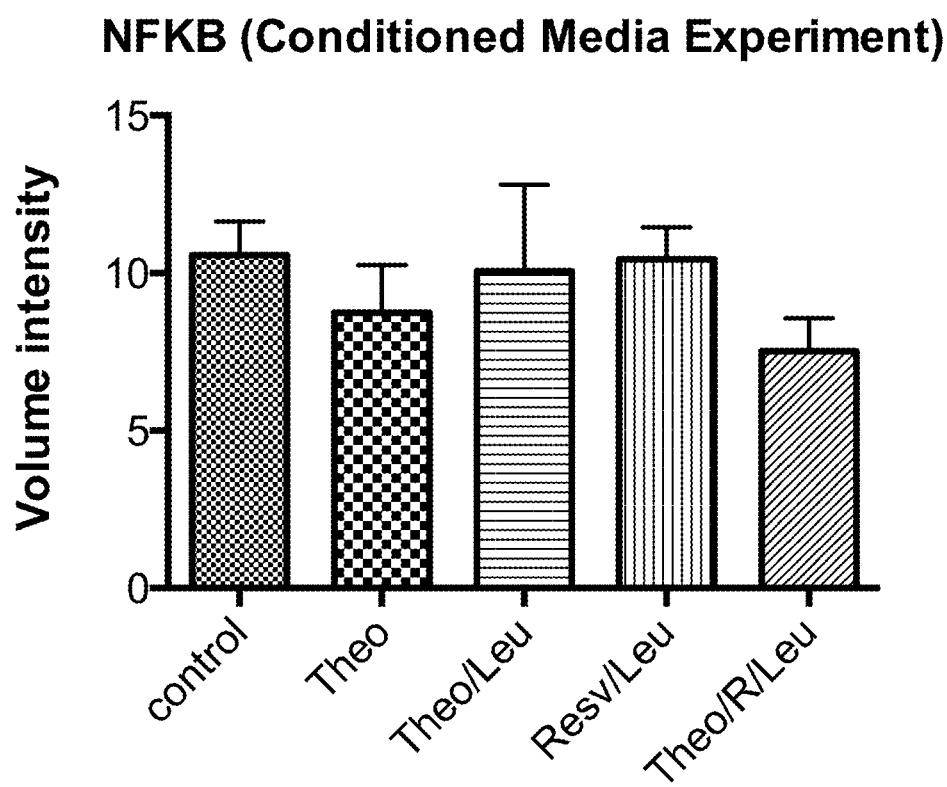
FIG. 2 depicts the interactive effects of theophylline with leucine and resveratrol (200 nM) conditioned adipocyte media on NFκB protein expression in mouse lung endothelial cells.
Figure 3:
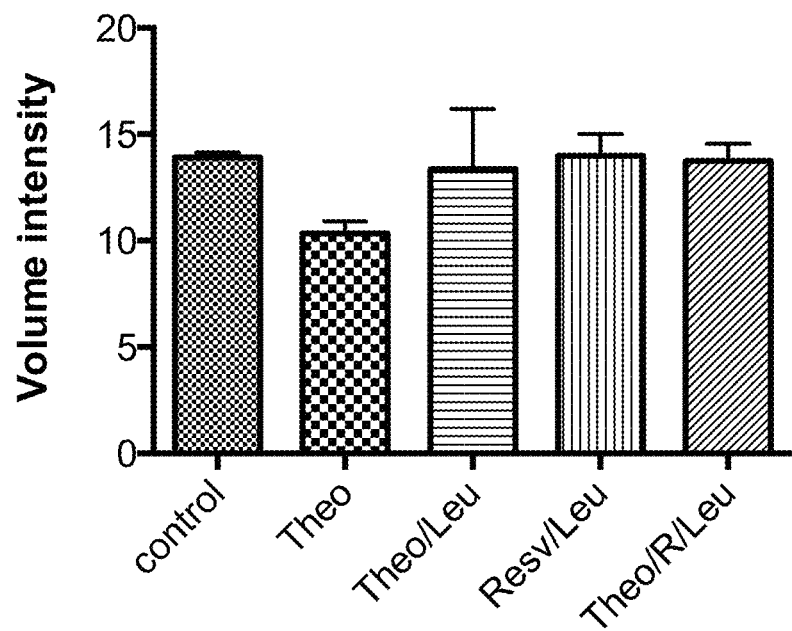
FIG. 3 depicts the interactive effects of theophylline with leucine and resveratrol conditioned adipocyte media on phospho-NFκB protein expression in mouse lung endothelial cells.

These effects on NFκB and phospho-NFκB were not recapitulated in the conditioned media experiments (FIG. 2 and FIG. 3), indicating that these are direct effects on MLEC and not mediated by alterations in cytokine secretion by adipocytes. The conditioned media experiments utilized media prepared from adipocytes treated with a control, theophylline, theophylline/leucine, resveratrol/leucine, and theophylline/resveratrol/leucine at the concentrations indicated above.

Figure 4:
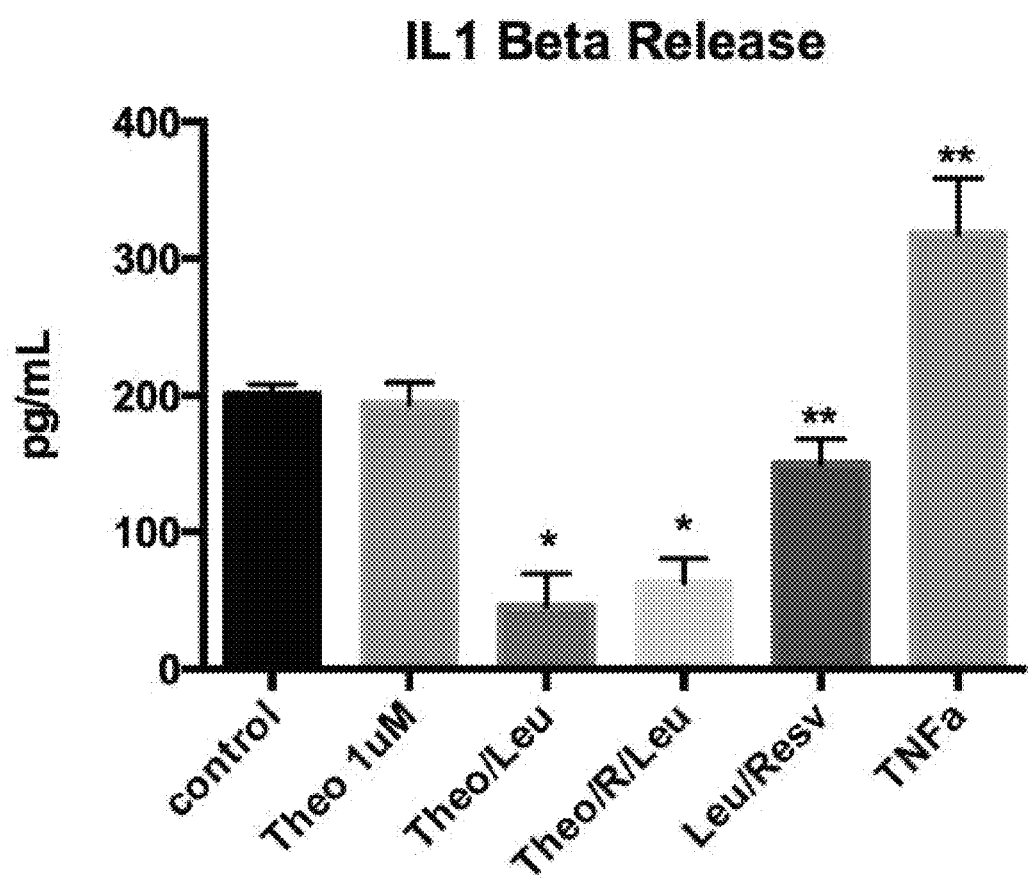
FIG. 4 depicts the interactive effects of theophylline with leucine and resveratrol on IL1-β from mouse lung endothelial cells. *p<0.001 vs. all other treatments. TNFα used as a positive control to stimulate secretion of the cytokine; **indicates significant increase vs. all other treatments (p<0.01).

In contrast, although this low concentration of theophylline exerted no significant independent effect on any of the inflammatory mediators studied, the leucine/theophylline and leucine/theophylline/resveratrol combinations resulted in marked reductions (~70%), relative to control, in IL1-β secretion ($p<0.001$; FIG. 4), with a smaller reduction found with the leucine/resveratrol combination in the absence of theophylline ($p<0.01$). TNFα used as a positive control to stimulate secretion of the cytokine, and an increase in IL1-β secretion was observed when MLEC was treated with TNFα ($p<0.01$).

As can be seen in FIG. 4, the combined treatment of theophylline with (a) leucine or (b) leucine and resveratrol yielded a synergistic effect on IL1-β secretion. Treatment with theophylline alone had no effect relative to the control and treatment with leucine/resveratrol had an effect of about 20% relative to control. In comparison, the combined treatment of theophylline with (a) leucine or (b) leucine and resveratrol had an improvement of about 70% relative to baseline. In this case, the synergistic effect is at least about 50% relative to the control.

Figure 5:
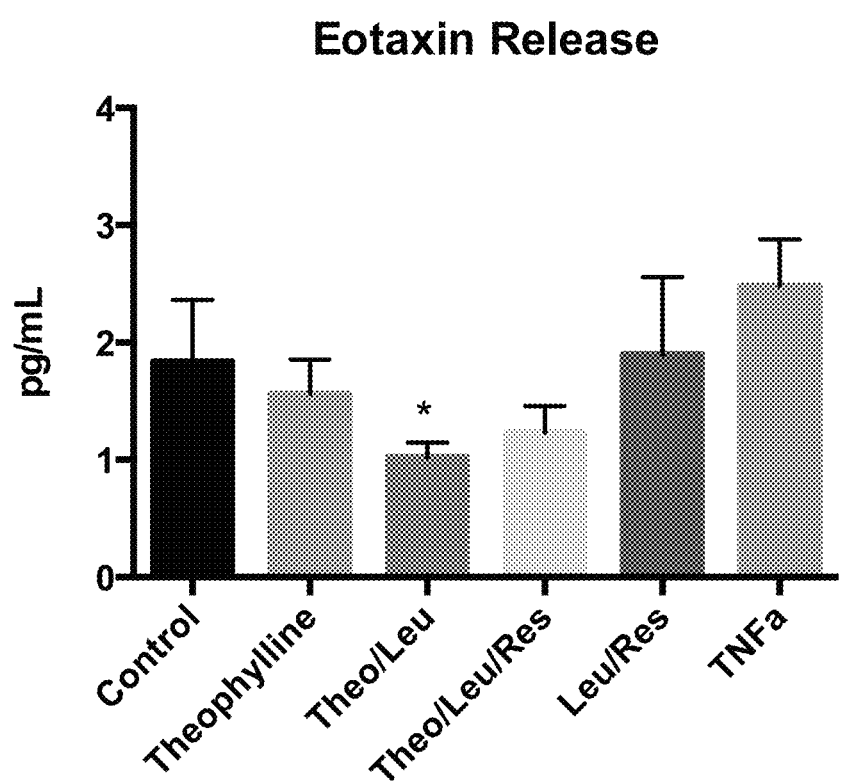
FIG. 5 depicts the interactive effects of theophylline with leucine and resveratrol on eotaxin secretion from mouse lung endothelial cells. *p<0.05 vs. all other treatments. TNFα used as a positive control to stimulate secretion of the cytokine

Similarly, the leucine/theophylline combination elicited a significant 44% decrease in the secretion of the chemokine eotaxin into the media, relative to control, ($p<0.05$; FIG. 5), while the other treatments (theophylline alone, theophylline/leucine/resveratrol, leucine resveratrol, and TNFα) exerted no significant effect. As can be seen here, the combined treatment of theophylline/leucine had a synergistic effect of at least about 70% on eotaxin secretion, relative to the control.

Figure 6:
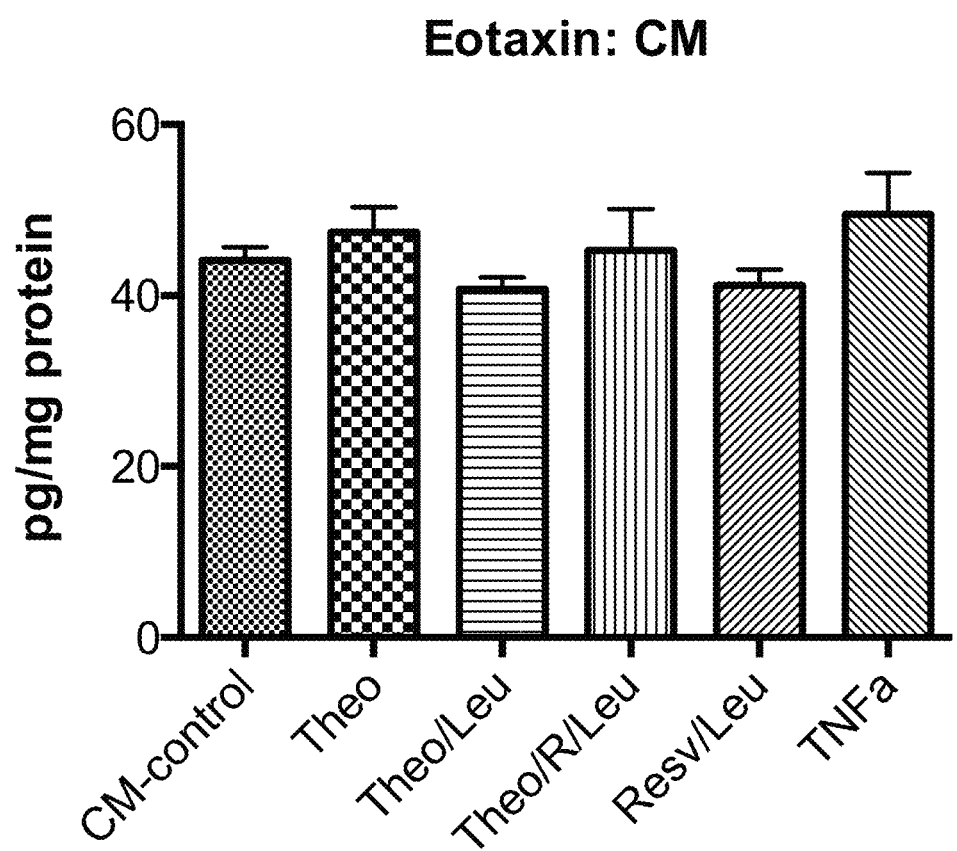
FIG. 6 depicts the interactive effects of theophylline with leucine and resveratrol conditioned adipocyte media on eotaxin secretion from mouse lung endothelial cells.

The effects shown in FIG. 5 are a direct effect on MLEC, as the conditioned media experiments produced no significant effect on eotaxin (FIG. 6).

Figure 7:
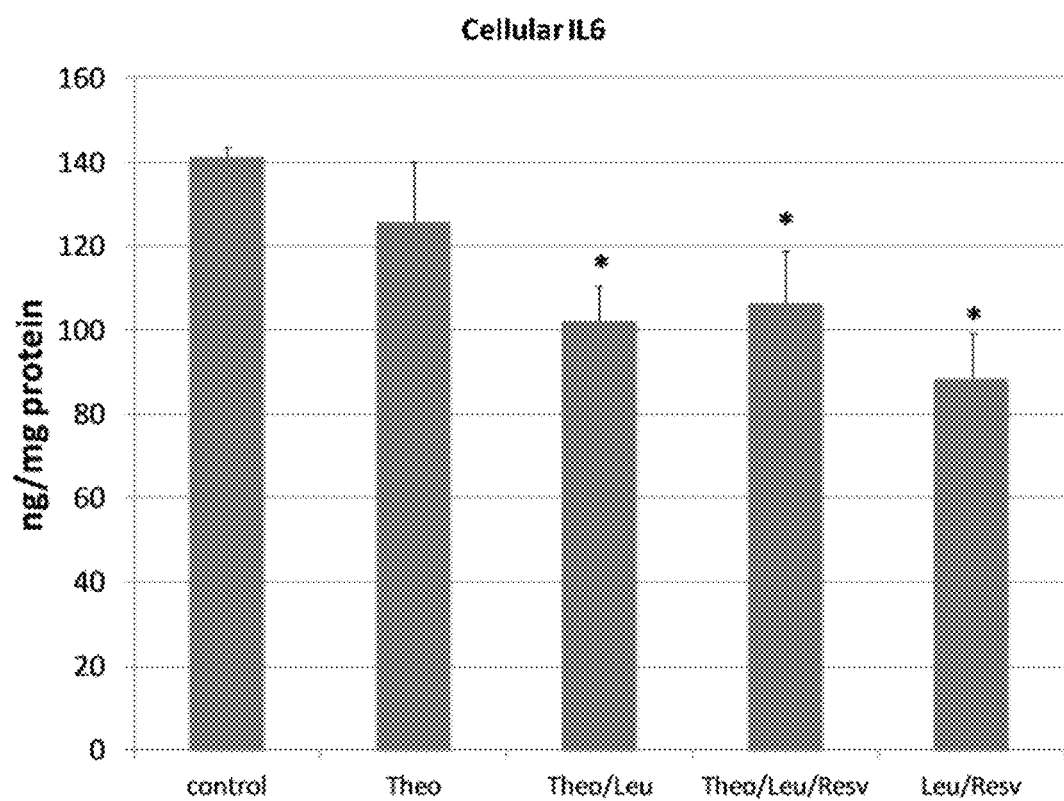
FIG. 7 depicts the interactive effects of theophylline with leucine and resveratrol on cellular IL 6 content in mouse lung endothelial cells. *p<0.02 vs. control.

Cellular expression of IL 6 was unaffected by theophylline, but the theophylline/leucine and theophylline/leucine/resveratrol treatments caused modest, significant decreases ($p<0.02$; FIG. 7).

Figure 8:
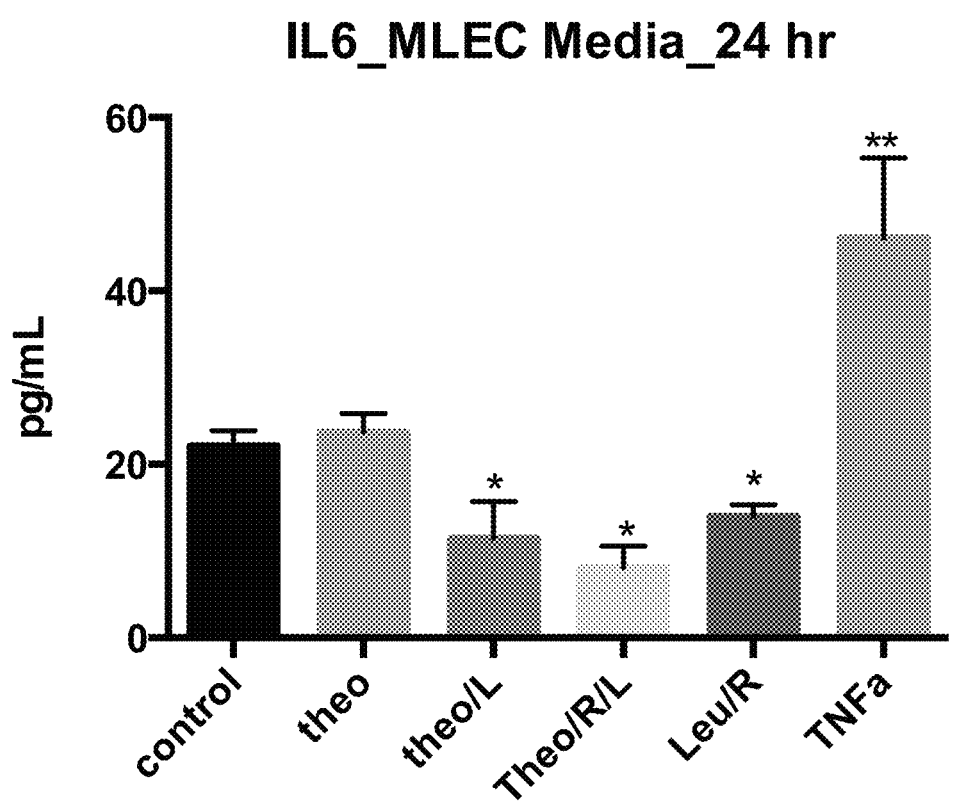
FIG. 8 depicts the interactive effects of theophylline with leucine and resveratrol on IL 6 secretion from mouse lung endothelial cells. *p<0.0001 vs. all other treatments. TNFα used as a positive control to stimulate secretion of the cytokine; ** indicates significant increase vs. all other treatments.

Similarly, IL 6 secretion into the media was decreased by ~50% by both the theophylline/leucine and theophylline/leucine/resveratrol treatments ($p<0.0001$; FIG. 8).

Figure 9:
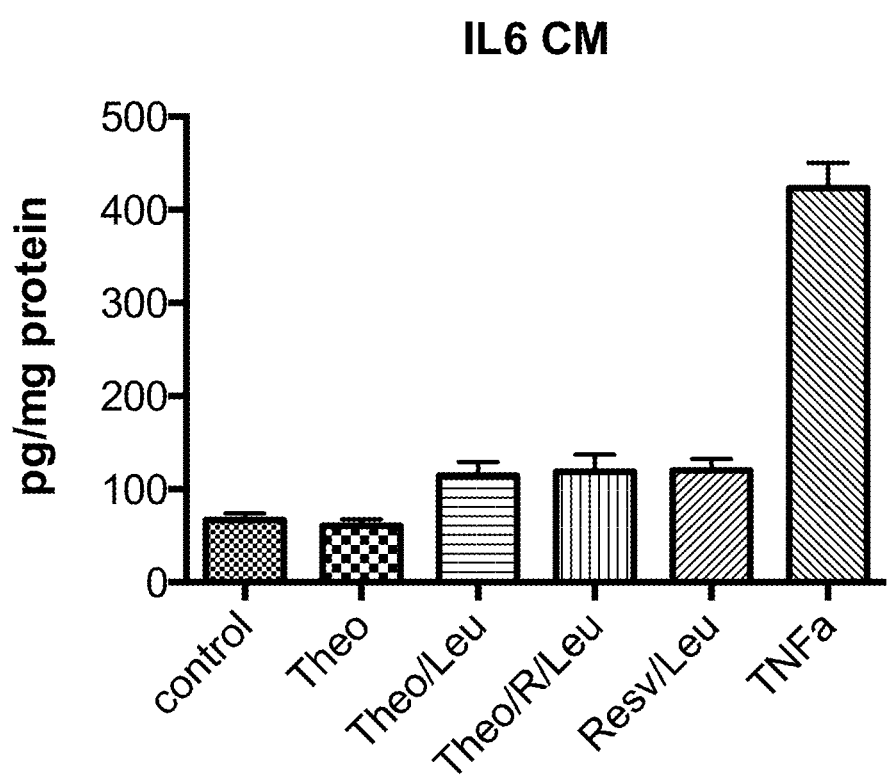
FIG. 9 depicts the interactive effects of theophylline with leucine and resveratrol conditioned adipocyte media on IL 6 secretion from mouse lung endothelial cells.

These direct effects were not recapitulated in the conditioned media experiments (FIG. 9), demonstrating that this anti-inflammatory effect is not mediated by alterations in adipocyte cytokine production.

Figure 10:
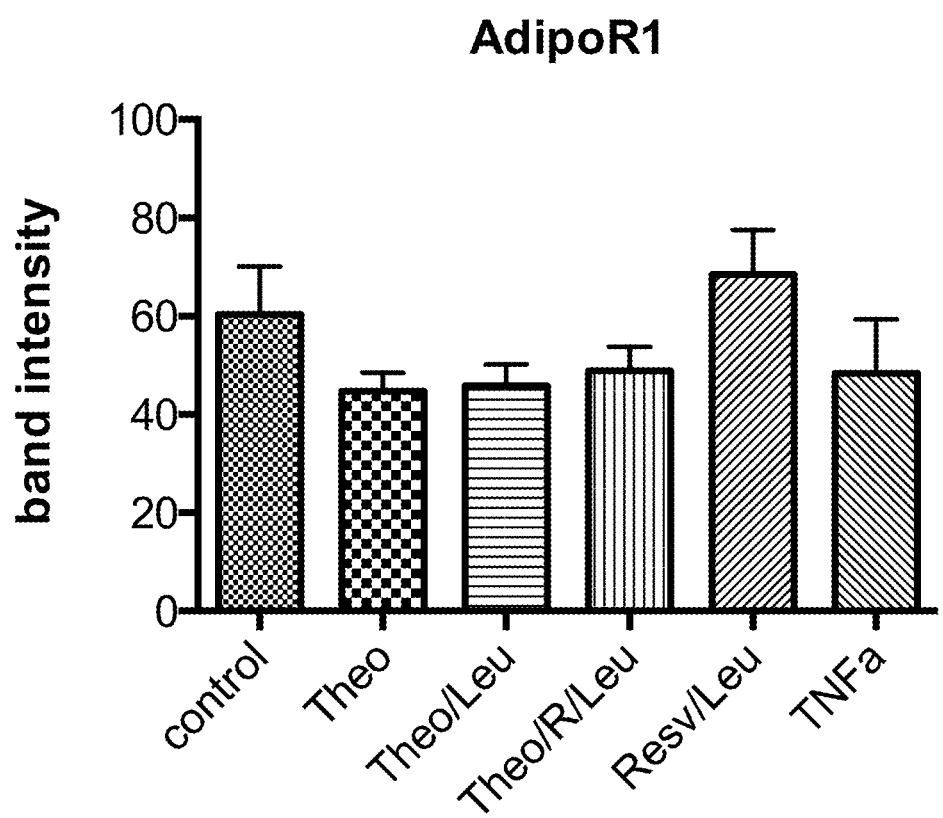
FIG. 10 depicts the interactive effects of theophylline with leucine and resveratrol on adiponectin receptor 1 protein expression in mouse lung endothelial cells.
Figure 11:
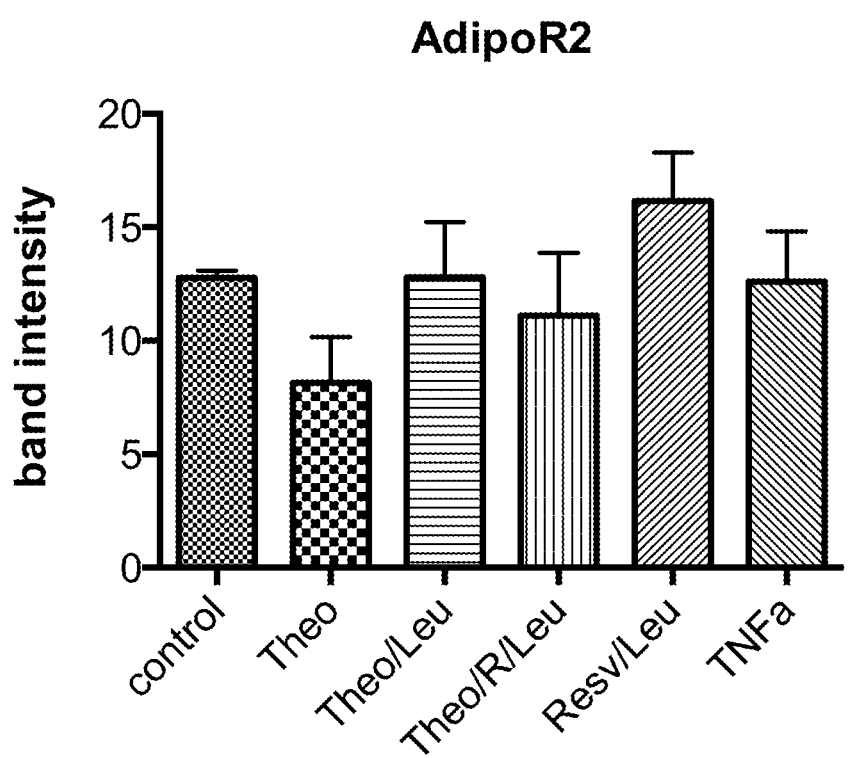
FIG. 11 depicts the interactive effects of theophylline with leucine and resveratrol on adiponectin receptor 2 protein expression in mouse lung endothelial cells.

There was no direct effect of any of the treatments on MLEC expression of either adiponectin receptor-1 (FIG. 10) or adiponectin receptor 2 (FIG. 11).

Figure 12:
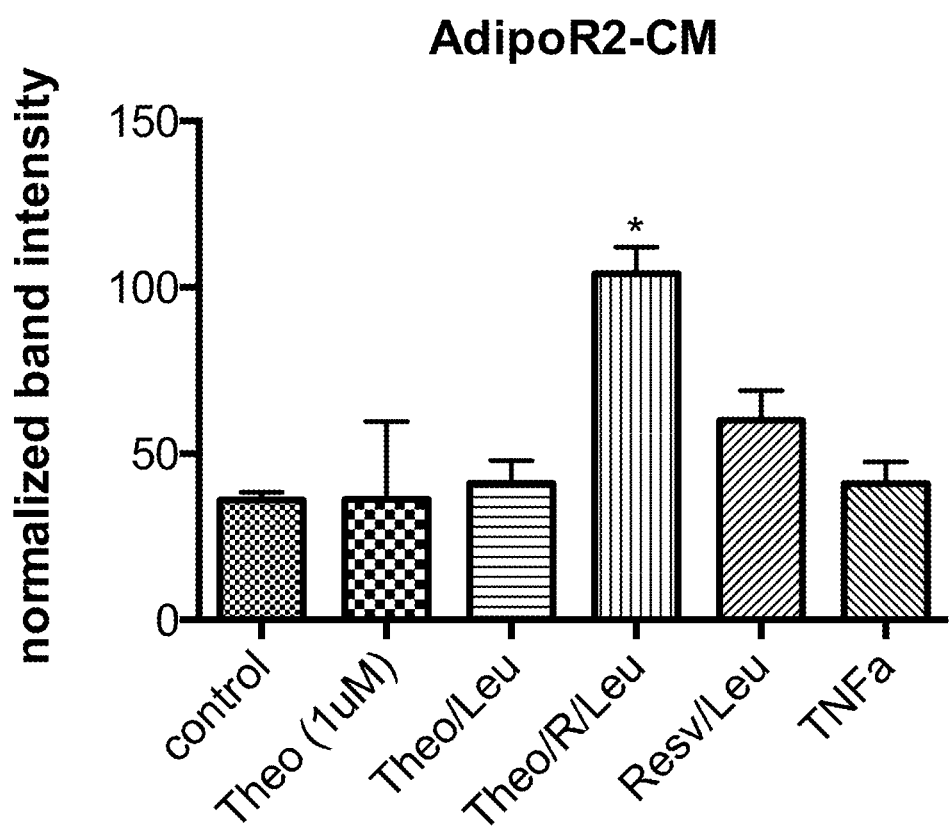
FIG. 12 depicts the interactive effects of theophylline with leucine and resveratrol conditioned adipocyte media on adiponectin receptor 2 protein expression in mouse lung endothelial cells. *p=0.018 vs. all other treatments.

However, treatment of adipocytes with the theophylline/leucine/resveratrol combination produced conditioned media that, when applied to MLEC, elicited a marked increase in the expression of the anti-inflammatory adiponectin-2 receptor in MLEC (p=0.0018, FIG. 12). As can be seen in FIG. 12, only treatment with theophylline/resveratrol/leucine yielded an improvement relative to control, suggesting a synergistic effect between all three components. For this combination, the synergistic effect was about 100%.

Figure 13:
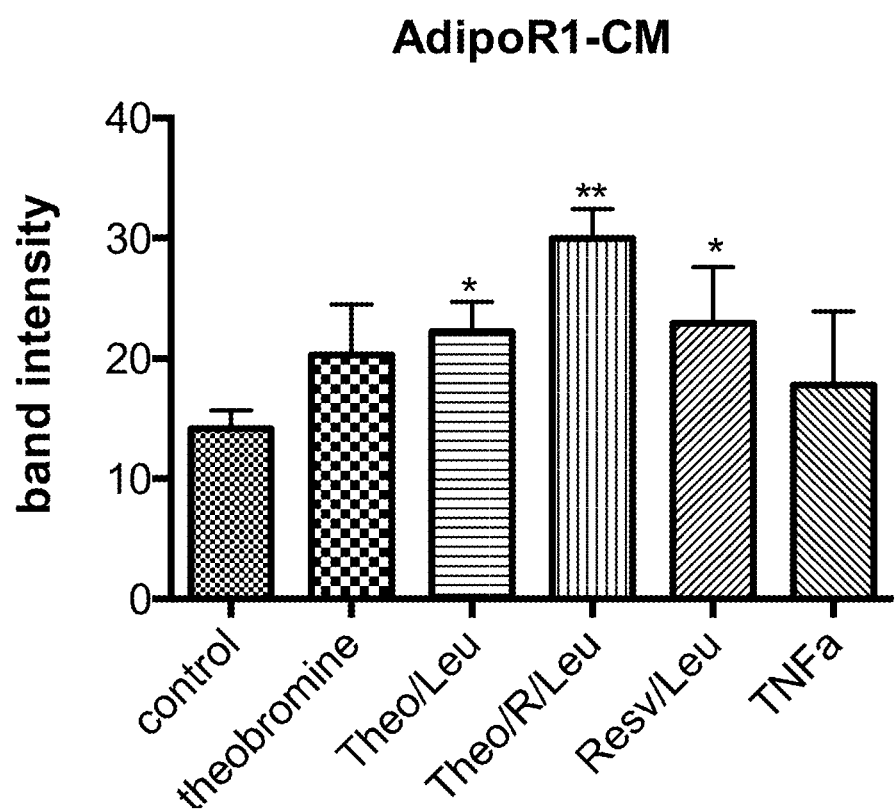
FIG. 13 depicts the interactive effects of theobromine with leucine and resveratrol conditioned adipocyte media on adiponectin receptor 1 protein expression in mouse lung endothelial cells. *p=0.03 vs. all other treatments; **p=0.0005 vs. all other treatments.

Similarly, when the theophylline was replaced with theobromine, another methylxanthine/non-specific PDE inhibitor, the theobromine/leucine and leucine/resveratrol combinations stimulated modest, significant increases in adiponectin receptor 1 (p<0.03, FIG. 13), with a further, more robust increase with the theobromine/leucine/resveratrol combination (p<0.0005, FIG. 13).

Figure 14:
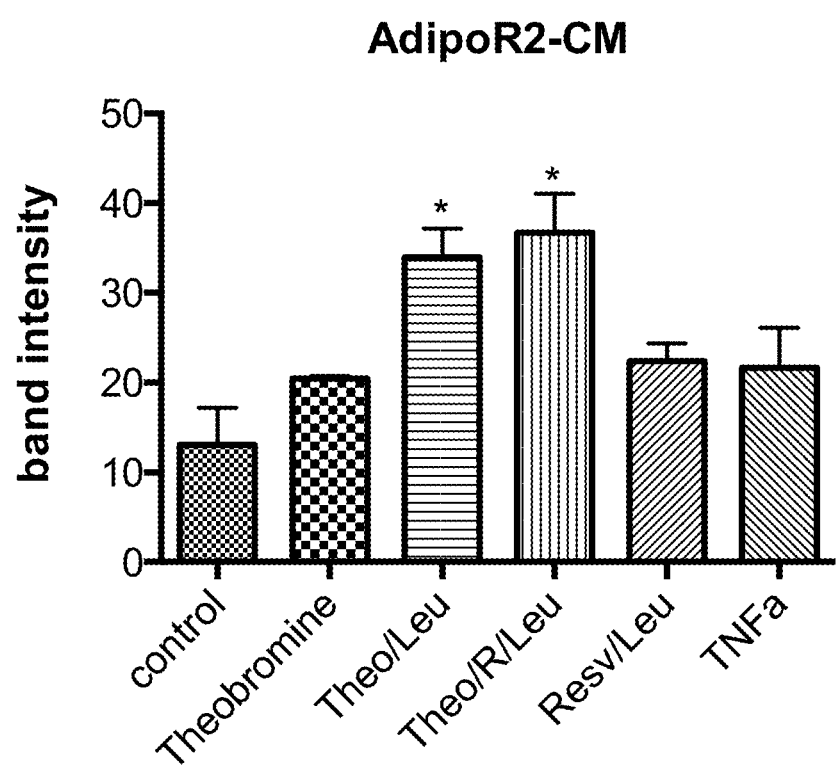
FIG. 14 depicts the interactive effects of theobromine with leucine and resveratrol conditioned adipocyte media on adiponectin receptor protein expression in mouse lung endothelial cells. *p=0.0001 vs. all other treatments.

Both the theobromine/leucine and theobromine/leucine/resveratrol combinations stimulated robust increases in adiponectin receptor 2 expression (p<0.0001, FIG. 14). As seen in FIG. 14, the combination of theobromine with either leucine or leucine/resveratrol yielded a synergistic effect of about 100%.

These data demonstrate significant synergy between the non-specific PDE inhibitors theophylline and theobromine with leucine in attenuating the inflammatory responses that result in airway diseases, including asthma and promoting anti-inflammatory responses. Notably, these effects are achieved at otherwise subtherapeutic doses of theophylline (1-2% of therapeutically effective levels).

Example 2

Effects of Administration of Leucine and Theophylline to Adult Female Balb/c Mice Techniques The interactive effects of leucine and theophylline was evaluated in sixty young adult female Balb/c mice that were randomized to the following six groups (n=10/group):

Group 1 was an untreated control group that was administered a diet containing a baseline level of leucine at 12 g of leucine/day.

Group 2 was a positive control group that was administered dexamethasone via IP injection and a diet containing a baseline level of leucine at 12 g of leucine/day.

Group 3 was administered a diet containing a high level of leucine (diet containing leucine at 12 g/day for days 0-13 and 24 g/day beginning on day 14) and no theophylline or dexamethasone.

Group 4 was administered sub-therapeutic level of theophylline (1 mg/kg theophylline, 10% of therapeutic level) via IP injection and a high leucine diet (diet containing leucine at 12 g/day for days 0-13 and 24 g/day beginning on day 14).

Group 5 was administered sub-therapeutic level of theophylline (3 mg/kg of theophylline, 30% of therapeutic level) via IP injection and a high leucine diet (diet containing leucine at 12 g/day for days 0-13 and 24 g/day beginning on day 14).

Group 6 was administered a therapeutic level of theophylline group that was administered 10 mg/kg of theophylline (100% of therapeutic level) along with a diet containing a baseline of leucine at 12 g of leucine/day.

The dosing and diet for each group is set out in further detail in the table below.

| Group Number | Group Size | Description | Diet | Route | Dose Level (mg/kg) | Volume Dosage (ml/kg) | Dosing Regime |
|---|---|---|---|---|---|---|---|
| 1 | n = 10 | Vehicle/Untreated control | 12 g Leucine diet | IP | NA | 10 ml/kg | Once daily on days 14-27 |
| 2 | n = 10 | Dexamethasone/Positive control | 12 g Leucine diet | IP | 10 mg/kg | 10 ml/kg | Once daily on days 25 to 27 |
| 3 | n = 10 | Vehicle/High Leucine | 12 g Leucine diet from day 0-13, thereafter switch to 24 g Leucine diet on day 14 | IP | NA | 10 ml/kg | Once daily on days 14-27 |
| 4 | n = 10 | 10% Theophylline | | IP | 1 mg/kg | 10 ml/kg | |
| 5 | n = 10 | 30% Theophylline | | IP | 3 mg/kg | 10 ml/kg | |
| 6 | n = 10 | 100% Theophylline/Baseline Leucine | 12 g Leucine diet | IP | 10 mg/kg | 10 ml/kg | |

Study length was 28 days, and asthma was induced via ovalbumin (OVA) sensitization on days 0 and 14 via IP injection, followed by intranasal OVA challenge on days 14 and 25-27.

Animals were sacrificed on day 28, subjected to bronchial alveolar lavage and the lavage fluid (BALF, 2 mL) and lungs collected. Airway inflammation was evaluated by assessing cellularity of BALF via flow cytometer; parameters used for cellular differentiation were sized granularity, autofluorescence and the expression of the following markers: CD45, Gr-1, CD11b, CCR3, B220 and CD3.

Cell types were defined as follows:
Eosinophils: $CD45^+$; Non-autofluorescent; $CCR3^+$.
Neutrophils: $CD45^+$; Non-autofluorescent; $Gr-1^+$; $CCR3^+$.
T cells: $CD45^+$; Non-autofluorescent; $Gr-1^-$; $CD3^+$.
B cells: $CD45^+$; Non-autofluorescent; $Gr-1^-$; $B220^+$.
Macrophages: $CD45^+$ autofluorescent: $CD11b^+$.

The non-cellular fraction of the BALF was analyzed for levels of IL-4, IL-5 and IL-13.

Results

Figure 15:
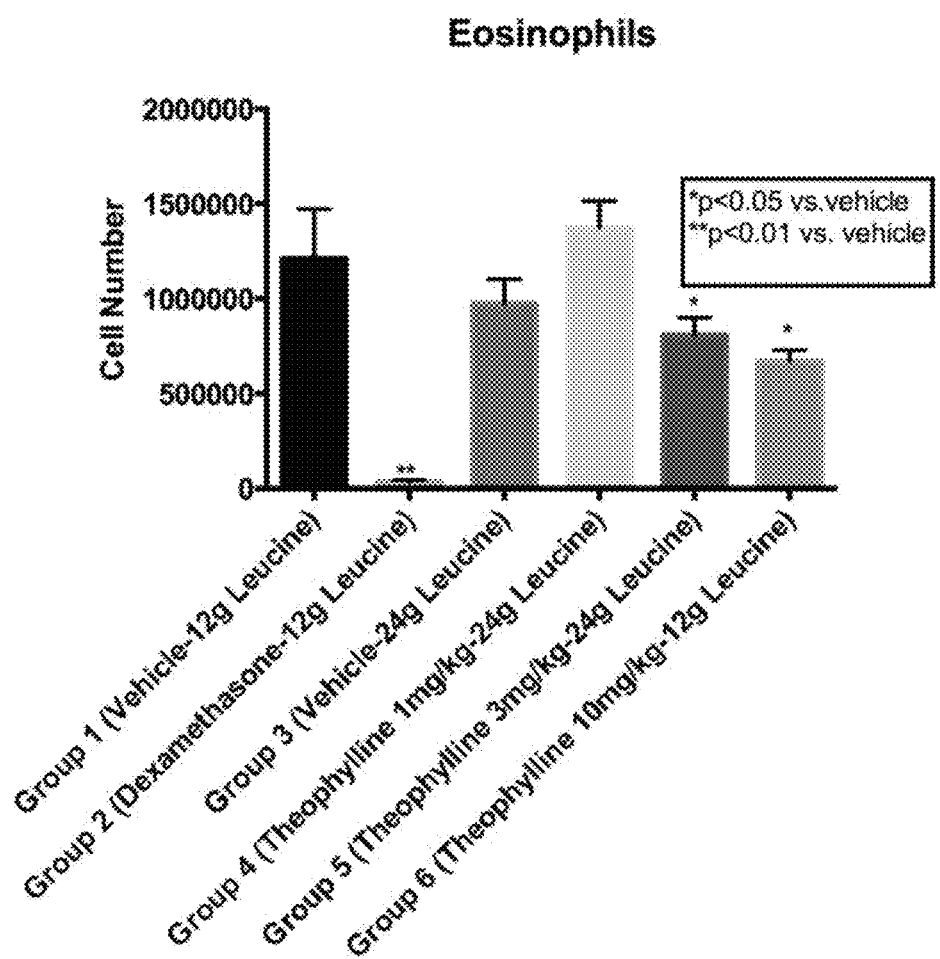
FIG. 15 depicts the interactive effects of administration of leucine and theophylline on eosinophil cell number in adult female Balb/c mice.

Administration of the steroid (dexamethasone) significantly reduced BALF total cellularity as well as eosinophil, neutrophil, T-cell and B-cell number. Therapeutic levels of theophylline (10 mg/kg) resulted in modest significant decreases in eosinophil number, and the combination of leucine with 3 mg/kg theophylline exerted a comparable effect, as shown in FIG. 15.

Figure 16:
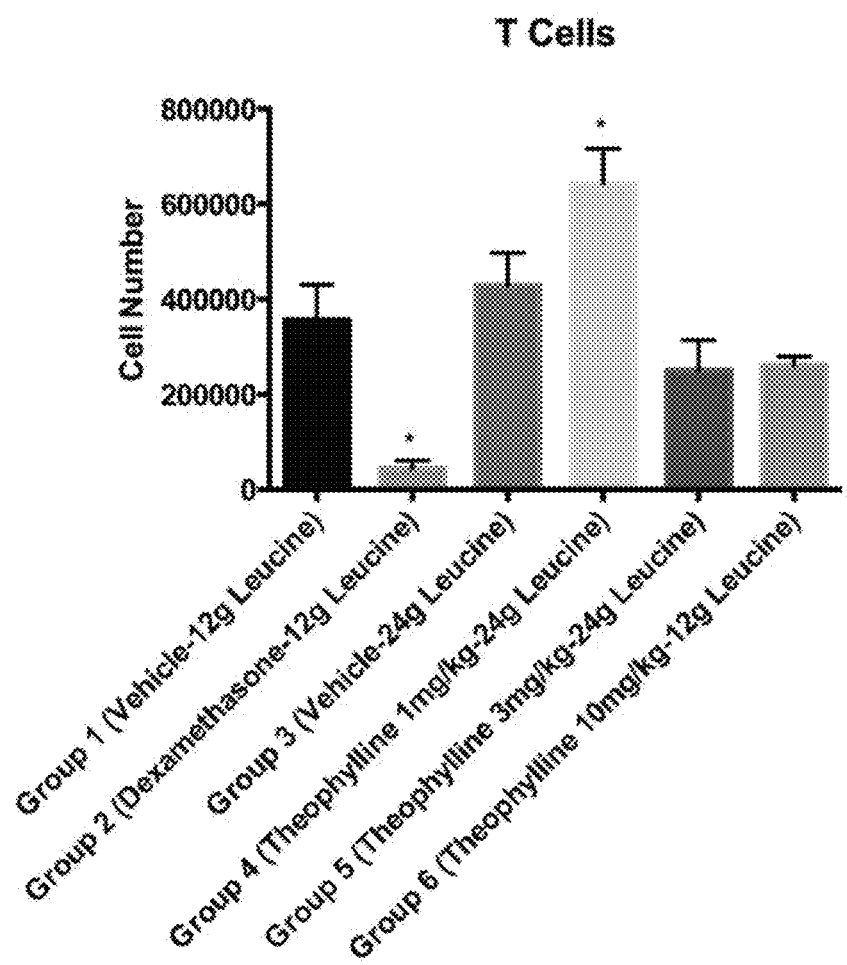
FIG. 16 depicts the interactive effects of administration of leucine and theophylline on T-cell number in adult female Balb/c mice.

Both therapeutic theophylline and leucine combined with 3 mg/kg theophylline modestly reduced T-cell number to a comparable degree, but this trend did not reach significance for either treatment ($0.05 < p < 0.1$). The lowest level of theophylline (1 mg/kg) combined with theophylline resulted in an increase in T-cells. These data are summarized in FIG. 16.

Figure 17:
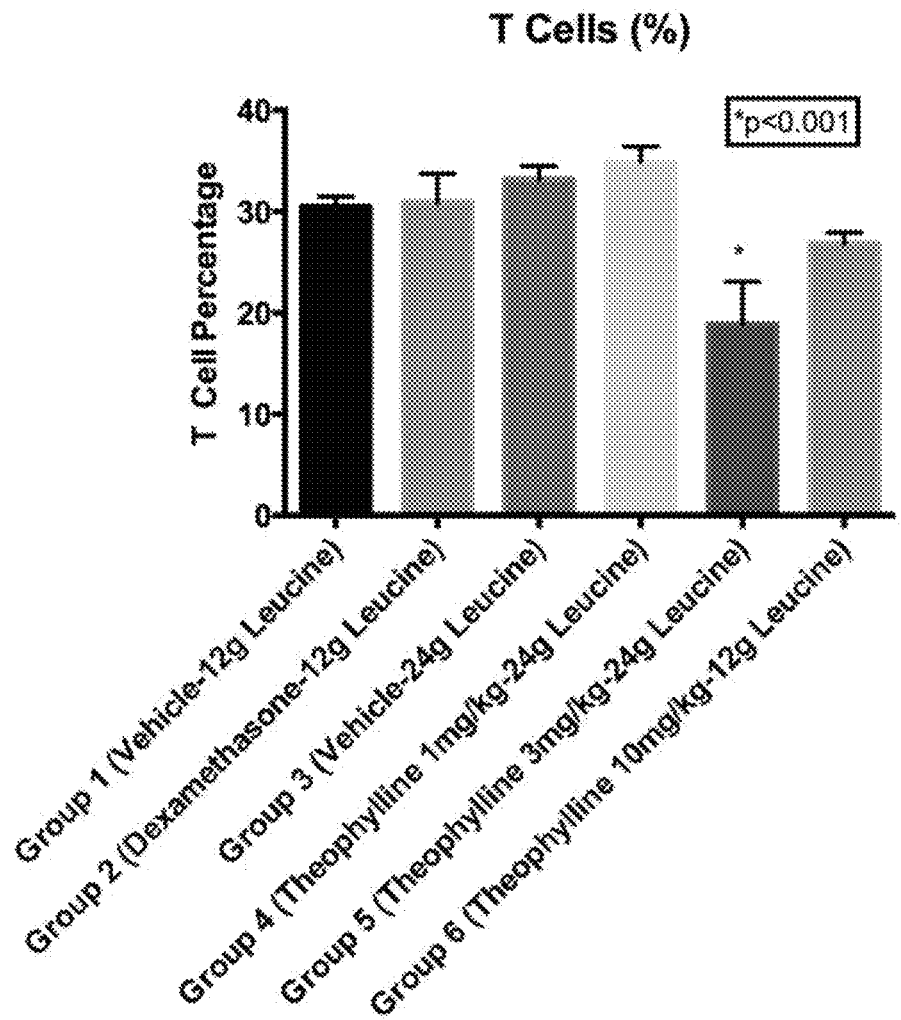
FIG. 17 depicts the interactive effects of administration of leucine and theophylline on the T-cell percentage in adult female Balb/c mice.

However, the combination of leucine with subtherapeutic theophylline (3 mg/kg) did significantly reduce the percentage of T cells in the BALF, as shown in FIG. 17.

The treatments exerted no significant effect on IL-4, IL-5 or IL-13.

These data indicate that leucine combined with a sub-therapeutic dose of theophylline attenuates the lymphocyte-mediated immune response in OVA-induced asthmatic mice.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A pharmaceutical composition comprising:
   (a) leucine and/or one or more leucine metabolites selected from the group consisting of keto-isocaproic acid (KIC), alpha-hydroxy-isocaproic acid, and hydroxymethylbutyrate (HMB); and
   (b) a methylxanthine;
   wherein the composition comprises at least 250 mg of leucine and/or between 10-200 mg of the one or more leucine metabolites;
   wherein the composition comprises 1-80 mg of the methylxanthine; and
   wherein the composition consists of the active ingredients (a), (b), and optionally resveratrol, and optionally pharmaceutically acceptable excipients.

2. The composition of claim 1, further comprising resveratrol.

3. The composition of claim 2, wherein the composition comprises at least 35 mg of resveratrol.

4. The composition of claim 2, wherein the composition comprises between 5-500 mg of resveratrol.

5. The composition of claim 1, wherein the composition comprises at least 500 mg of leucine.

6. The composition of claim 1, wherein the composition comprises between 250-1500 mg of leucine.

7. The composition of claim 1, wherein the composition comprises 10-100 mg of leucine metabolites.

8. The composition of claim 1, wherein the composition comprises between 100-200 mg of leucine metabolites.

9. The composition of claim 1, wherein the methylxanthine is selected from the group consisting of theophylline and theobromine.

10. The composition of claim 9, wherein the compositions comprises at least 5 mg of theophylline.

11. The composition of claim 9, wherein the composition comprises 1-25 mg of theophylline.

12. The composition of claim 1, wherein the composition comprises 1-50 mg of methylxanthine.

13. The composition of claim 1, wherein the composition is a unit dosage.

14. The composition of claim 1, wherein the composition comprising an amino acid consisting of leucine.

15. The composition of claim 1, wherein the composition further comprises pharmaceutically acceptable excipients.

16. A pharmaceutical composition comprising:
   (a) leucine and/or between 10-200 mg of one or more leucine metabolites selected from the group consisting of keto-isocaproic acid (KIC), alpha-hydroxy-isocaproic acid, and hydroxymethylbutyrate (HMB); and
   (b) a methylxanthine;
   wherein the mass ratio of (a) to (b) is at least 15,
   wherein the composition comprises between 5-80 mg of the methylxanthine, and
   wherein the composition consists of the active ingredients (a), (b), and optionally resveratrol, and optionally pharmaceutically acceptable excipients.

17. The composition of claim 16, further comprising at least 10 mg of resveratrol.

18. The composition of claim 16, wherein the methylxanthine is theophylline or theobromine.

19. The composition of claim 16, wherein the composition is formulated as a unit dosage.

20. A pharmaceutical composition comprising:
   (a) leucine and/or between 10-200 mg of one or more leucine metabolites selected from the group consisting of keto-isocaproic acid (KIC), alpha-hydroxy-isocaproic acid, and hydroxymethylbutyrate (HMB); and
   (b) a methylxanthine;
   wherein the molar ratio of (a) to (b) is at least 400, 500, 750, or 1000,
   wherein the composition comprises between 0.05 µg-80 mg of the methylxanthine; and
   wherein the composition consists of the active ingredients (a), (b), and optionally resveratrol, and optionally pharmaceutically acceptable excipients.

21. The composition of claim 20, further comprising at least 0.01 µg of resveratrol.

22. The composition of claim 20, wherein the methylxanthine is theophylline or theobromine.

23. The composition of claim 20, wherein the composition is formulated as a unit dosage.

24. A method of treating chronic obstructive pulmonary disease (COPD) or asthma in a subject in need of treatment comprising administering to the subject the composition of claim 1.

25. A method of treating chronic obstructive pulmonary disease (COPD) or asthma in a subject in need of treatment comprising administering to the subject the composition of claim 1, wherein administering the composition to the subject increases expression level or secretion of an inflammatory marker in a lung endothelial cell selected from the group consisting of NFKB, eotaxin, IL1-β, and IL6, or reducing expression level or secretion of one or more anti-inflammatory markers in a lung endothelial cell selected from the group consisting of adiponectin receptor 1 and adiponectin receptor 2.

* * * * *